(12) United States Patent
Jang et al.

(10) Patent No.: US 9,880,183 B2
(45) Date of Patent: Jan. 30, 2018

(54) METHOD FOR CONTROLLING A TEST APPARATUS IN RESPONSE TO EXTERNAL ROOM CONDITIONS AND REACTION DEVICE STORAGE CONDITIONS

(71) Applicant: SAMSUNG ELECTRONICS CO., LTD., Suwon-si (KR)

(72) Inventors: Eun Jeong Jang, Suwon-si (KR); Sung Hwa Lee, Anyang-si (KR); Jung Tae Lee, Suwon-si (KR); Jeong Min Jo, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

(21) Appl. No.: 14/932,322

(22) Filed: Nov. 4, 2015

(65) Prior Publication Data

US 2016/0187362 A1 Jun. 30, 2016

(30) Foreign Application Priority Data

Dec. 30, 2014 (KR) ........................ 10-2014-0193555

(51) Int. Cl.
*G01N 35/00* (2006.01)
*B01L 7/00* (2006.01)

(52) U.S. Cl.
CPC .......... *G01N 35/00871* (2013.01); *B01L 7/00* (2013.01); *G01N 35/00069* (2013.01); *G01N 35/0092* (2013.01); *G01N 35/00712* (2013.01); *B01L 2200/147* (2013.01); *B01L 2300/027* (2013.01); *G01N 2035/0091* (2013.01); *G01N 2035/00346* (2013.01); *G01N 2035/00435* (2013.01); *G01N 2035/00455* (2013.01); *G01N 2035/00851* (2013.01)

(58) Field of Classification Search
CPC ...................................... G01N 35/00
USPC .................................. 422/63–67; 436/43–55
See application file for complete search history.

(56) References Cited

U.S. PATENT DOCUMENTS

| 8,318,094 | B1 * | 11/2012 | Bayandorian | ........ G01N 21/645 422/400 |
| 2002/0054828 | A1 * | 5/2002 | Keeping | .................. G01N 1/14 422/63 |
| 2004/0053290 | A1 * | 3/2004 | Terbrueggen | ....... B01F 11/0071 435/6.11 |
| 2005/0207936 | A1 * | 9/2005 | Berryhill | ............ B01D 53/9495 422/63 |
| 2006/0030049 | A1 * | 2/2006 | Bhimani | ............... B01L 3/0206 436/43 |

(Continued)

FOREIGN PATENT DOCUMENTS

CN 202994794 * 6/2013
KR 10-2014-0099345 A 8/2014

*Primary Examiner* — Arlen Soderquist
(74) *Attorney, Agent, or Firm* — Sughrue Mion, PLLC

(57) ABSTRACT

A test apparatus and a method for controlling the same are provided. The test apparatus may receive information about a reaction device, information about a storage environment, and external environment information from a storage storing a sample and a sensor sensing the external environment of the test apparatus. The test apparatus may perform a variety of control actions for testing the sample based on a temperature of and around the reaction device, resulting in increased reliability of the test result.

26 Claims, 24 Drawing Sheets

(56) References Cited

U.S. PATENT DOCUMENTS

| | | | |
|---|---|---|---|
| 2007/0116600 A1* | 5/2007 | Kochar | G01N 21/76 422/65 |
| 2008/0031774 A1* | 2/2008 | Magnant | B01L 3/5085 422/63 |
| 2008/0202927 A1* | 8/2008 | Kayyem | B01L 3/502 204/403.01 |
| 2011/0165688 A1* | 7/2011 | Dupoteau | A61B 5/1172 436/55 |
| 2011/0236981 A1* | 9/2011 | Wakamiya | G01N 35/00663 436/52 |
| 2013/0078624 A1* | 3/2013 | Holmes | C12Q 1/00 435/6.11 |
| 2015/0004717 A1* | 1/2015 | McDevitt | G01N 35/00029 436/501 |

* cited by examiner

METHOD FOR CONTROLLING A TEST APPARATUS IN RESPONSE TO EXTERNAL ROOM CONDITIONS AND REACTION DEVICE STORAGE CONDITIONS

CROSS-REFERENCE TO RELATED APPLICATION(S)

This application claims priority from Korean Patent Application No. 10-2014-0193555, filed on Dec. 30, 2014 in the Korean Intellectual Property Office, the entire disclosure of which is incorporated herein by reference.

BACKGROUND

1. Field

Apparatuses and methods consistent with exemplary embodiments relate to a test apparatus and a method for controlling the same, which can perform in-vitro diagnosis using small samples.

2. Description of the Related Art

To perform in-vitro diagnosis, various tests, for example, an immune test, a clinical chemical test, gene analysis, and the like, are performed on samples of patients. These tests are very important as they may be used to diagnose and cure a disease of which a patient is afflicted as well as observe prognosis thereof.

In-vitro diagnosis may be performed by a reaction device in which a sample reacts with a reagent and a test apparatus that obtains a result of the in-vitro diagnosis result by measuring a reaction that occurs in the reaction device.

When the test apparatus obtains the result of the diagnosis, a storage temperature of a sample and a reaction temperature of the sample are important to the in-vitro diagnosis result, and. Accordingly, a precise temperature control is important for acquiring an accurate result and ultimately in making an accurate diagnosis.

SUMMARY

Exemplary embodiments overcome the above disadvantages and other disadvantages not described above. Also, an exemplary embodiment is not required to overcome the disadvantages described above, and an exemplary embodiment may not overcome any of the problems described above.

One or more exemplary embodiments herein provide a test apparatus for receiving information regarding a reaction device from both a storage storing a sample therein and a sensor sensing the external environment of the test apparatus, information about the storage environment, and information about the external environment. Accordingly, the test apparatus may perform various control actions for testing the sample base on the received information, thereby increasing a reliability of the test result.

Additional aspects will be set forth in part in the description which follows and, in part, will be obvious from the description, or may be learned by practice of the invention.

According to an aspect of an exemplary embodiment, provided is a test apparatus including a communicator configured to receive at least one of storage time information of a reaction device and storage environment information from a storage including the reaction device therein, and receive external environment information of the test apparatus from an external sensor, and a controller configured to determine whether testing of the reaction device is to be performed based on at least one of the storage time information of the reaction device, the environment information of the storage, and the external environment information of the test apparatus.

The storage environment information may include at least one of internal temperature information and humidity information of the storage.

The external environment information may include at least one of external temperature information and humidity information of the test apparatus.

The controller may estimate at least one of a temperature and a humidity of the reaction device based on the storage time information of the reaction device, the storage environment information, and the external environment information.

The controller may compare at least one of the estimated temperature and humidity of the reaction device with a predetermined reference value, and determine whether the estimated at least one of temperature and humidity of the reaction device is within a reference range.

The test apparatus may further include a display configured to display a warning screen image in response to at least one of the estimated temperature and humidity of the reaction device exceeding the reference range.

The controller may prevent testing of the reaction device in response to at least one of temperature and humidity of the reaction device exceeding the reference range.

The controller may prevent testing of the reaction device in response to at least one of an external temperature and humidity of the reaction device exceeding a reference range.

The controller may control an internal temperature of the test apparatus to be a temperature appropriate for a test process applied to the reaction device based on the estimated reaction device temperature.

The controller may determine a storage state of the reaction device based on the storage time information of the reaction device and the storage environment information, and prevent testing of the reaction device in response to the storage state of the reaction device being inappropriate.

The controller may determine an exposed time of the reaction device and information about the exposed external environment based on the storage time information of the reaction device and the external environment information.

The test apparatus may further include a display configured to display the exposed time of the reaction device and the information about the exposed external environment.

The controller may compare information about a recommended storage environment of the reaction device stored in the storage with the storage environment information, and determine whether the storage environment information matches the recommended storage environment.

The controller may transmit a control signal for controlling at least one of a temperature and a humidity of the storage to the storage, in response to the storage environment information not matching the recommended storage environment.

The controller may transmit a warning message to a pre-registered mobile device of a user in response to the storage environment information not matching the recommended storage environment.

The controller may transmit a control signal for controlling an external environment to an air-conditioner located externally from the test apparatus, in response to the external environment information exceeding a predetermined reference range.

The controller may control at least one of an internal temperature and a humidity of the test apparatus in a standby state based on the external environment information.

The receiver may further be configured to receive information about the reaction device that may include at least one of identification (ID) information of the reaction device, information about a recommended storage environment of the reaction device, and information about a test process applied to the reaction device.

The test apparatus may further include a reader configured to, in response to the reaction device being inserted into a storage of the test apparatus, obtain the reaction device information from a tag attached to the inserted reaction device.

According to an aspect of another exemplary embodiment, provided is a test apparatus for testing a reaction occurring in a reaction device including a communicator configured to receive information about a recommended storage environment of the reaction device and storage environment information from a storage storing the reaction device therein, and a controller configured to determine whether the storage environment information matches a recommended storage environment of the reaction device.

The controller may transmit a control signal for controlling at least one of a temperature and a humidity of the storage to the storage, in response to the storage environment information not matching the recommended storage environment of the reaction device.

The controller may transmit a warning message to a pre-registered mobile device of a user in response to the storage environment information not matching the recommended storage environment of the reaction device.

According to an aspect of another exemplary embodiment, provided is a method for controlling a test apparatus including acquiring information of a reaction device, receiving at least one of storage time information of the reaction device and storage environment information from a storage storing the reaction device therein, and receiving external environment information of the test apparatus from an external sensor, and determining whether testing of the reaction device is to be performed based on at least one of the storage time information of the reaction device, the environment information of the storage, and the external environment information of the test apparatus.

The reaction device information may include at least one of identification (ID) information of the reaction device, information about a recommended storage environment of the reaction device, and information about a test process applied to the reaction device.

The storage environment information may include at least one of internal temperature information and humidity information of the storage.

The external environment information may include at least one of external temperature information and humidity information of the test apparatus.

The determining whether testing of the reaction device is to be performed may include estimating at least one of a temperature and a humidity of the reaction device based on the storage time information of the reaction device, the storage environment information, and the external environment information.

The determining whether testing of the reaction device is to be performed may include comparing at least one of the estimated temperature and humidity of the reaction device with a predetermined reference value, and determining whether at least one of temperature and humidity of the reaction device is in a reference range.

The method may further include displaying a warning screen image in response to at least one of the estimated temperature and humidity of the reaction device exceeding the reference range.

The method may further include preventing testing of the reaction device in response to at least one of temperature and humidity of the reaction device exceeding the reference range.

The method may further include, in response to determining testing of the reaction device is to be performed, controlling an internal temperature of the test apparatus to be a temperature appropriate for a test process applied to the reaction device based on the estimated temperature of the reaction device.

The determining whether testing of the reaction device is to be performed may include determining a storage state of the reaction device based on the storage time information of the reaction device and the storage environment information.

The determining whether testing of the reaction device is to be performed may include determining an exposed time of the reaction device and information about the exposed external environment based on the storage time information of the reaction device and the external environment information.

The acquiring the reaction device information may include, in response to the reaction device being inserted into the test apparatus, acquiring the reaction device information from a tag attached to the inserted reaction device.

BRIEF DESCRIPTION OF THE DRAWINGS

These and/or other aspects will be more apparent and more readily appreciated from the following description of the exemplary embodiments, taken in conjunction with the accompanying drawings, in which.

DETAILED DESCRIPTION

Figure 1:
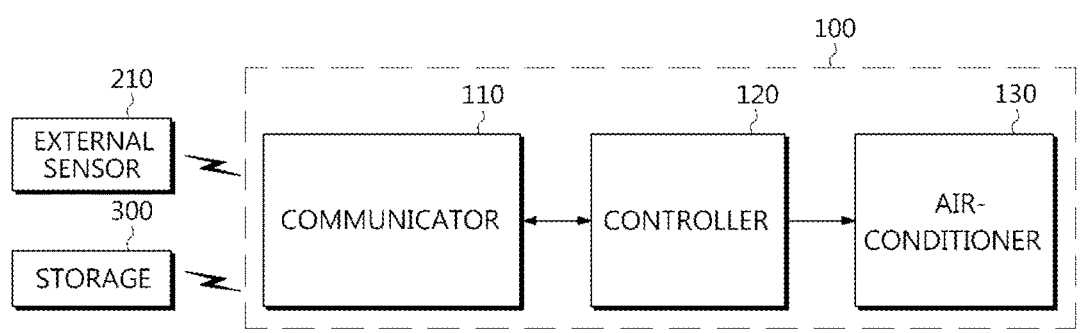
FIG. 1 is a block diagram illustrating a test apparatus according to an exemplary embodiment.

Reference will now be made in detail to the exemplary embodiments which are illustrated in the accompanying drawings, wherein like reference numerals refer to like elements throughout.

The features described herein may be embodied in different forms, and are not to be construed as being limited to the examples described herein. Rather, the examples described herein have been provided so that this disclosure will be thorough and complete, and will convey the full scope of the disclosure to one of ordinary skill in the art. The drawings may not be to scale, and the relative size, proportions, and depiction of elements in the drawings may be exaggerated for clarity, illustration, and convenience.

For in-vitro diagnosis, various tests, for example, an immune test, a clinical chemical test, gene analysis, and the like, may be used according to categories of samples or target materials. Generally, when a sample reacts with a reagent under an environment similar to the internal environment of a human, human enzymes may become activated, and the most accurate results may be acquired. In addition, when gene analysis is performed using the sample, the sample may be heated to a high or low temperature for a short time so as to amplify genes in such a manner that precise temperature control is needed. As a non-limiting example, gene analysis may be performed using polymerase chain reaction (PCR) which requires a repeated heating and cooling of a sample mixture, to thereby map a human genome.

Therefore, according to various exemplary embodiments, the test apparatus and method described herein may communicate with an external temperature sensor and a storage apparatus so as to accurately and precisely control temperature. Accordingly, the test apparatus may transmit/receive signals to/from the external temperature sensor and the storage. Exemplary structures and operations thereof are further described herein.

FIG. 1 is a block diagram illustrating a test apparatus according to an exemplary embodiment.

Referring to FIG. 1, the test apparatus 100 includes a communicator 110, a controller 120, and an air-conditioner 130. The communicator 110 may transmit/receive information by communicating with an external sensor 210 and a storage 300. The controller 120 may control at least one of an internal temperature or humidity of the test apparatus 100, an external temperature or humidity of the test apparatus 100, and a temperature or humidity of the storage 300. Also, the controller 120 may determine whether the reaction device is to be tested. The air-conditioner 130 may control the internal temperature or humidity of the test apparatus 100.

The communicator 110 may include at least one of a Bluetooth communication module for communicating with a single external device on a one-to-one basis or for communicating with a small number of external devices on a one-to-multiple basis, a Wireless Fidelity (Wi-Fi) communication module for connecting to a local area network (LAN) through an access point (AP) or the like, and a near field communication (NFC) module, such as a ZigBee communication module, that may be used to form a local area network (LAN) between the external sensor 210 and the storage 300.

While the communication module contained in the communicator 110 may include a Bluetooth communication module, a Wi-Fi communication module, and a near field communication (NFC) module, the exemplary embodiments are not limited thereto, and the communication module may also include other communication modules for performing communication according to various communication protocols.

The external sensor 210 may detect at least one of a temperature and humidity of a space in which the test apparatus 100 is located, and may transmit the detected temperature and/or humidity to the communicator 110. Here, the term "external" may refer to the external environment of the test apparatus 100.

The storage 300 may store the reaction device that is to be tested by the test apparatus 100. A reagent for reacting with a sample of the patient may be included in the reaction device. Generally, the reaction devices are stored at a temperature that is lower than room temperature. Accordingly, the storage 300 may be a type of refrigerator. The storage 300 may transmit the environment information such as the internal temperature or humidity and information about the stored reaction device to the communicator 100 of the test apparatus 100.

The controller 120 may control at least one of the internal temperature or humidity of the test apparatus 100, the external temperature or humidity of the test apparatus 100, and the temperature or humidity of the storage 300, based on information received from the external sensor 210 and the storage 300, and determine whether the test apparatus can be tested. For example, to control the internal temperature or humidity, a control signal may be applied to the air-conditioner 130. In response, the air-conditioner 130 may heat or cool the internal air of the test apparatus 100, or may control the internal humidity of the test apparatus 100, examples of which are further described herein.

Figure 2:
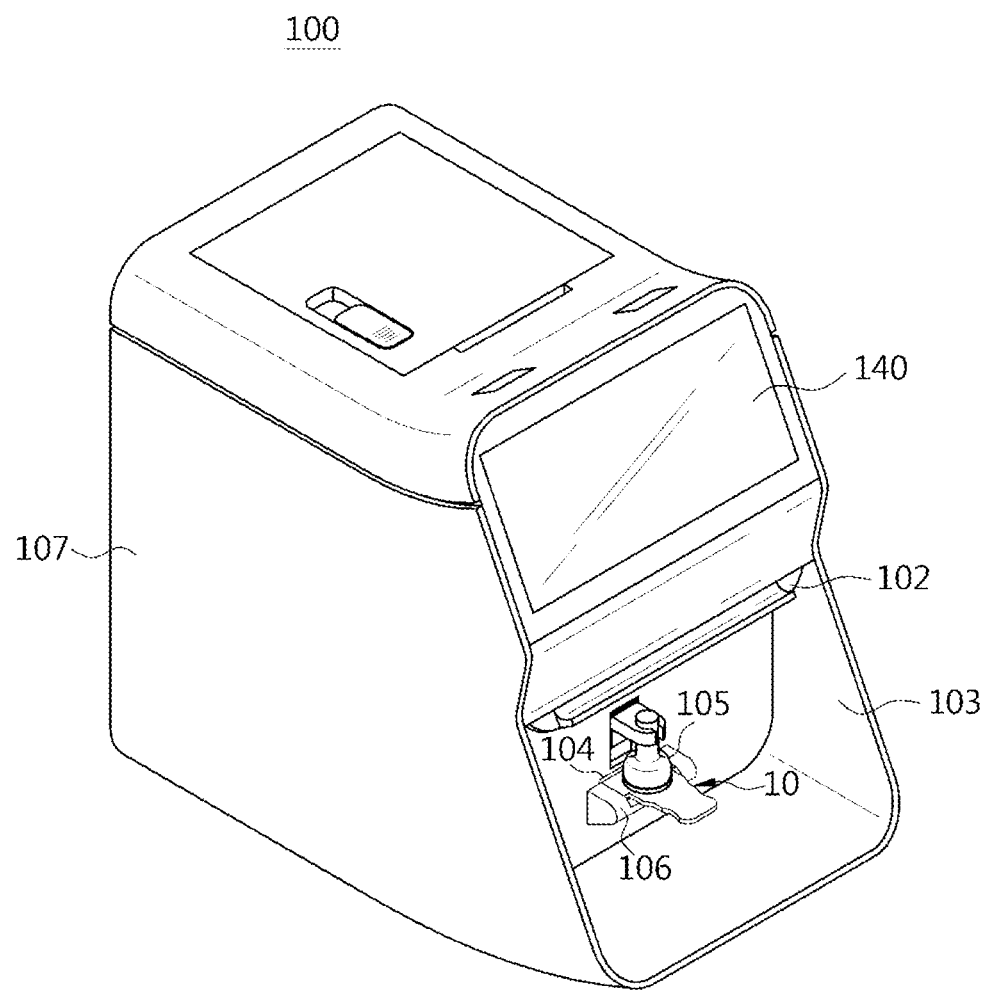
FIG. 2 illustrates the external appearance of a test apparatus according to an exemplary embodiment.
Figure 3:
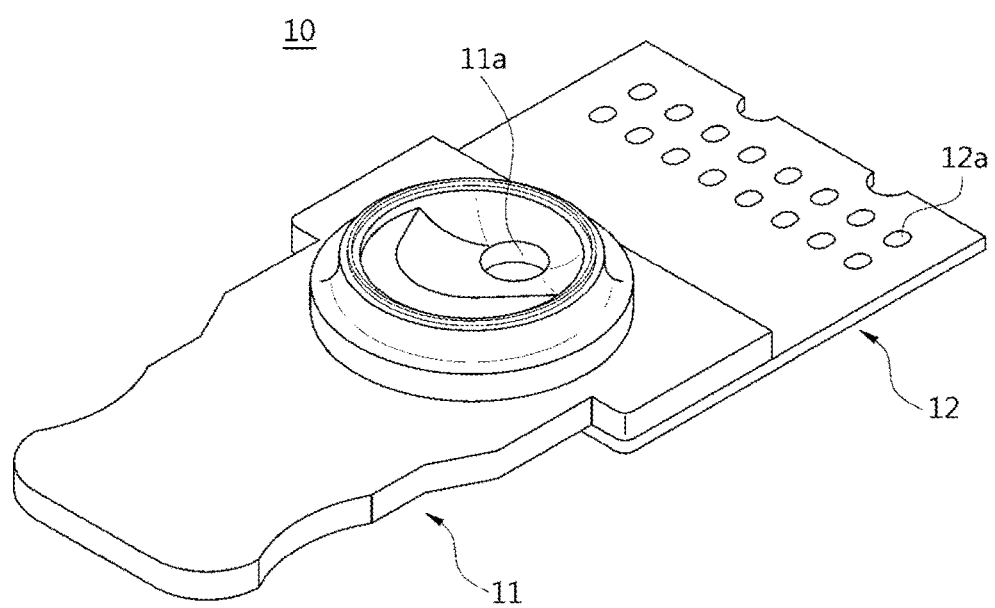
FIG. 3 illustrates the external appearance of a reaction device inserted into the test apparatus shown in FIG. 2 according to an exemplary embodiment.

FIG. 2 illustrates an external appearance of the test apparatus according to an exemplary embodiment. FIG. 3 illustrates the external appearance of a reaction device inserted into the test apparatus shown in FIG. 2 according to an exemplary embodiment.

The test apparatus 100 may be miniaturized and automated and be used for testing various kinds of samples, for example, environmental samples, bio-samples, food samples, and the like. For example, if the test apparatus 100 is used for in-vitro diagnosis for testing bio-samples collected from a human body, a Point of Care Testing (POCT) can be quickly carried out by users of the test apparatus 100 such as patients, doctors, nurses, and medical technologists in sites such as homes, offices, outpatient clinics, hospital rooms, emergency rooms, operating rooms and intensive care rooms, other than a central inspecting room.

There are a variety of reaction devices into which a sample may be inserted and caused to react with a reagent. As a non-limiting example, the reaction device may include a cartridge-type reaction device in which the sample or reagent moves by capillary force, a disc-type reaction device in which the sample or reagent moves by centrifugal force, a cuvette-type reaction device in which the sample or reagent does not move and measurement is immediately achieved, and the like. The structure or configuration of the test apparatus may be changed according to the above-mentioned reaction device types. FIG. 2 illustrates an example in which the test apparatus 100 has a cartridge-type reaction device 10 inserted therein.

Referring to FIG. 2, the test apparatus 100 includes a mounting unit 103, which is a space in which the reaction device 10 is installed, and the reaction device 10 which may be inserted into the test apparatus 100 after opening a door 102 of the mounting unit 103 through upward sliding. In particular, some parts of the reaction device 10 may be inserted into a predetermined insertion groove 104 arranged at the mounting unit 103.

Some parts of the reaction device 10 may be inserted into the main body 107, and the remaining parts may be exposed to an outside of the test apparatus 100 and may be supported by a support body 106. In addition, when a pressing unit 105 presses the reaction device 10, introduction of a sample into the test apparatus 100 may be accelerated.

If installation of the reaction device 10 is completed, the test apparatus 100 closes the door 102 and may begin testing.

In this example, the controller 120 and the air-conditioner 130 are embedded in the main body 107. For example, the controller 120 may include a main processor, a graphic processor, and a memory.

The memory may store a control program or control data for controlling operations of the test apparatus 100, and may temporarily store control command data that is generated from the main processor or image data that is generated from the graphics processor.

The memory may include at least one of a volatile memory and a non-volatile memory. For example, the volatile memory may include an SRAM or DRAM, and the non-volatile memory may include at least one of a flash memory, a ROM (Read Only Memory), an Erasable Programmable Read Only Memory (EPROM), an Electrically Erasable Programmable Read Only Memory (EEPROM), and the like.

The non-volatile memory may store a control program and control data to control various operations of the test apparatus 100. The volatile memory may retrieve the control program and control data from the non-volatile memory, may temporarily store the control program and control data therein. Also, the volatile memory may temporarily store control command data generated from the main processor or image data generated from the graphics processor.

The graphics processor may convert image data that is received from the main processor and image data stored in the memory into image data that is capable of being displayed by a display 140, and may transmit the converted image data to the display 140.

The main processor may process data stored in the memory according to a control program stored in the memory. For example, the main processor may generate a control signal used for controlling at least one of an internal temperature, an external temperature, and a temperature of the storage 300 based on information received from the external sensor 210 and the storage 300. Here, the main processor may be implemented as a single processor or a plurality of processors.

As another example, the cartridge-type reaction device configured to be inserted into the test apparatus 100 shown in FIG. 2 may have an appearance as shown in FIG. 3.

Referring to FIG. 3, the reaction device 10 includes a housing 11 and a platform 12 in which a sample reacts with a reagent. The housing 11 may support the platform 12 and may act as a handle to enable a user to grasp the reaction device 10. The platform 12 may be bonded to a lower part of the housing 11, or may be inserted into a predetermined groove that is formed in the housing 11, so that the platform 12 may be coupled to the housing 11.

The housing 11 may be formed by a material that is chemically and biologically inactive and that may be easily molded. For example, the housing 11 may be formed of various materials such as plastic materials including acryl, such as polymethylmethacrylate (PMMA), etc., polysiloxane, such as polydimethylsiloxane (PDMS), etc., polycarbonate (PC), polyethylene, such as linear low-density polyethylene (LLDPE), low-density polyethylene (LDPE), medium-density polyethylene (MDPE), high-density polyethylene (HDPE), etc., polyvinyl alcohol, very low density polyethylene (VLDPE), polypropylene (PP), acrylonitrile butadiene styrene (ABS), cycloolefin copolymer (COC), etc., glass, mica, silica, semiconductor wafer, and the like.

An inlet hole 11a in which the sample is inserted may be formed in the housing 11. For example, a user may drop the sample that is to be tested into the inlet hole 11a using a device such as pipet or syringe.

In this example, a plurality of chambers 12a are formed in the platform 12, and a reagent may be accommodated in each of the chambers 12a. For example, the reagent may be deposited into the chamber 12a and then dried. The sample inserted into the inlet hole 11a may arrive at the chamber 12a through a channel (not shown) that is configured to interconnect the inlet hole 11a and the chamber 12a, and may react with the reagent contained in the chamber 12a. In FIG. 2, some portions of the reaction device 10 may be inserted into the groove 104 of the test apparatus 100. Because the sample reacts with the reagent in the chamber 12a, the platform 12 may be inserted into the groove 104, and the pressing unit 105 presses the inlet hole 11a so that introduction of the sample may be accelerated.

Although not shown in the drawings, the platform 12 may be formed by bonding three plates to one another. In this example, the three plates may include an upper plate, a lower plate, and an intermediate plate. The upper plate and the lower plate may be printed with a light shielding ink, and may serve to protect the sample flowing into the chamber 12a from external light and from foreign substances.

The upper plate and the lower plate may take the form of films. For example, the films may be used to form the upper plate and the lower plate, and may be one or more selected from among a polyethylene film, such as a very low-density polyethylene (VLDPE) film, a linear low density polyethylene (LLDPE) film, a low-density polyethylene (LDPE) film, a medium-density polyethylene (MDPE) film, a high-density polyethylene (HDPE) film, etc., a polypropylene (PP) film, a polyvinylchloride (PVC) film, a polyvinyl alcohol (PVA) film, a polystyrene (PS) film, and a polyethylene terephthalate (PET) film.

In some examples, the intermediate plate may be a porous sheet, such as a cellulose sheet. Thus, the intermediate plate may serve as a vent. In this example, the porous sheet may be formed of a hydrophobic material, or may be subjected to hydrophobic treatment, thus having little or no effect on a movement of the sample.

As described above, when the platform 12 has a triple-layered structure, a hole constructing the inlet hole 11a may be formed in each of the upper plate and the intermediate plate, and portions corresponding to the chamber 12a of the upper plate and the lower plate may be transparent to enable measurement of optical properties caused by a reaction occurring in the chamber 12a.

A thin channel is formed in the intermediate plate, and the sample introduced through the inlet hole 11a may move to the chamber 12a by capillary force of the channel.

Figure 4:
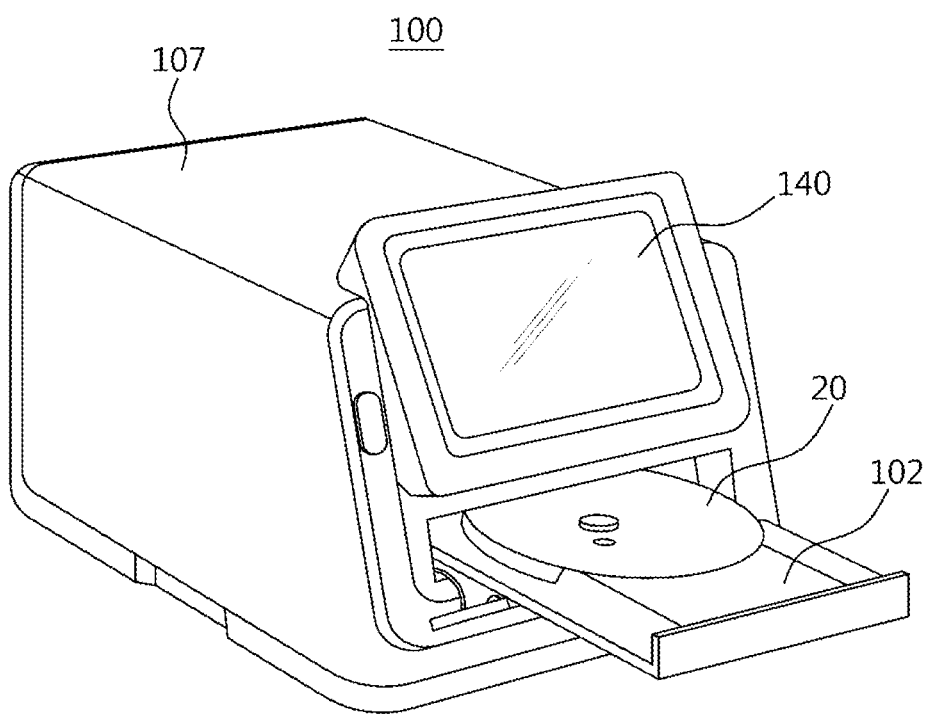
FIG. 4 illustrates the external appearance of a test apparatus according to another exemplary embodiment.
Figure 5:
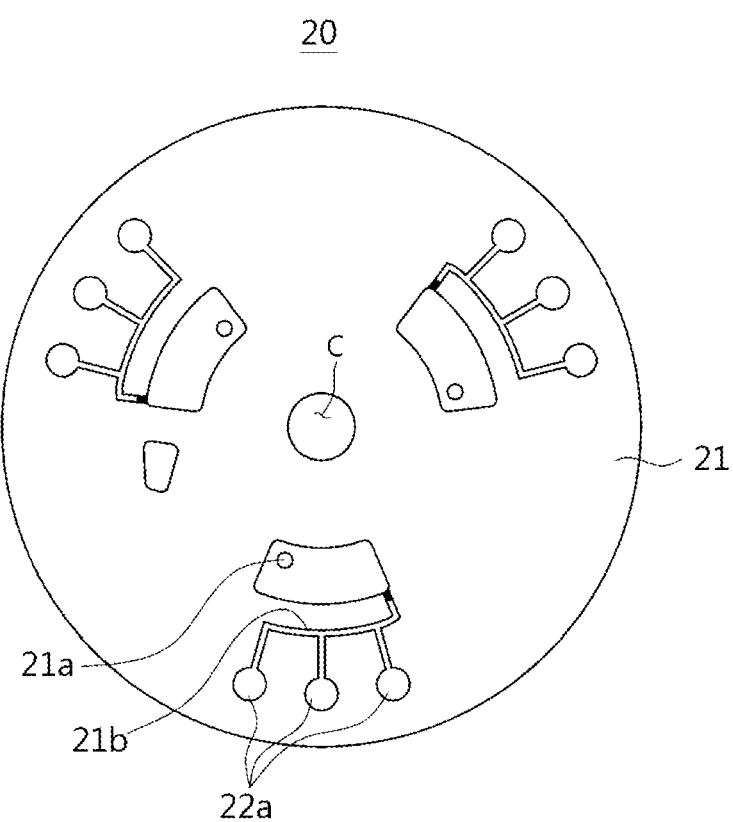
FIG. 5 illustrates the external appearance of a test apparatus shown in FIG. 4 according to an exemplary embodiment.

FIG. 4 illustrates the external appearance of a test apparatus according to another exemplary embodiment. FIG. 5 illustrates the external appearance of the test apparatus shown in FIG. 4 according to an exemplary embodiment.

FIG. 4 illustrates an example in which a disc-type reaction device is inserted into the test apparatus.

Referring to FIG. 4, a tray 102 onto which the disc-type reaction device 20 may be seated is included in the test apparatus 100. The seated reaction device 20 along with the tray 102 may be inserted into the main body 107 of the test apparatus 100. Once the reaction device 20 is inserted, the test apparatus 100 may rotate the reaction device 20 according to a sequence based upon a type of the inserted reaction device 20, a sample type, or a test process, and may measure the test result.

Referring to FIG. 5, the disc-type reaction device 20 may include a rotatable platform 21 and structures that are formed in the platform 21. The structures may include a plurality of chambers accommodating the sample and/or reagent and a channel for interconnecting the chambers. Although the structure is formed in the reaction device 20, the reaction device 20 may be formed of a transparent material so that a user can view the structures formed in the reaction device 20 from above.

The platform 21 may be formed of a biologically inactive material that may be easily molded. For example, the platform 21 may be formed of various materials such as plastic materials including acryl, such as polymethylmethacrylate (PMMA), etc., polydimethylsiloxane (PDMS), polycarbonate (PC), polypropylene (PP), polyvinyl alcohol (PVA), polyethylene (PE), etc., glass, mica, silica, silicon wafer, and the like.

However, the exemplary embodiments are not limited to the above examples and any material that has chemical and biological stability and mechanical processability may be used as a material for forming the platform 21. In addition, when test results of the reaction device 20 are optically analyzed, the platform 21 may further have optical transparency.

The platform 21 may form the inlet hole 21a in which the sample is inserted, a chamber 22a in which the reagent is accommodated, and a channel 21b for interconnecting the inlet hole 21a and the chamber 22a.

As already described in the example of FIG. 4, the test apparatus 100 may rotate the reaction device 20. If a turntable for applying a rotational force received from the test apparatus 100 is inserted into an intermediate hole (C) formed in the center of the reaction device 20, and the reaction device 20 is rotated, the sample received through the inlet hole 21a may move to the chamber 22a by centrifugal force. For example, if the sample is blood, the blood may be centrifugally separated by rotation. As an example, the platform 21 may further include a plurality of structures for centrifugation of the blood.

The disc-type reaction device may include a platform 21 formed of a plate including a plurality of layers. For example, if the platform 21 is formed of two plates, i.e., an upper plate and a lower plate, an intaglio structure that has a chamber or channel may be formed on a surface at which the upper plate contacts the lower plate. In this example, the two plates may be bonded to each other so that a space accommodating the fluids and a passage enabling the fluids to flow may be provided inside of the platform 101. Bonding between the plates may be carried out by a variety of methods, for example, adhesion using an adhesive or a double-sided tape, ultrasonic fusing, laser welding, and the like.

Meanwhile, the reaction devices (10, 20) shown in FIGS. 3 and 5 may enable quantitative analysis using only a small amount of a sample. In addition, the sample or reagent disposed in the reaction devices (10, 20) moves along the channel and is a fluid. Therefore, the reaction device 10 or 20 may be referred to as a microfluidic device.

The appearance or category of the test apparatus 100 is not limited only to the examples of FIGS. 2 and 4. As another example, a spectrometer for testing the cuvette-type reaction device may also be the test apparatus 100 according to the embodiment. Also, the test apparatus 100 may be any test apparatus that may be affected by the external temperature, the internal temperature, or the sample temperature.

Figure 6:
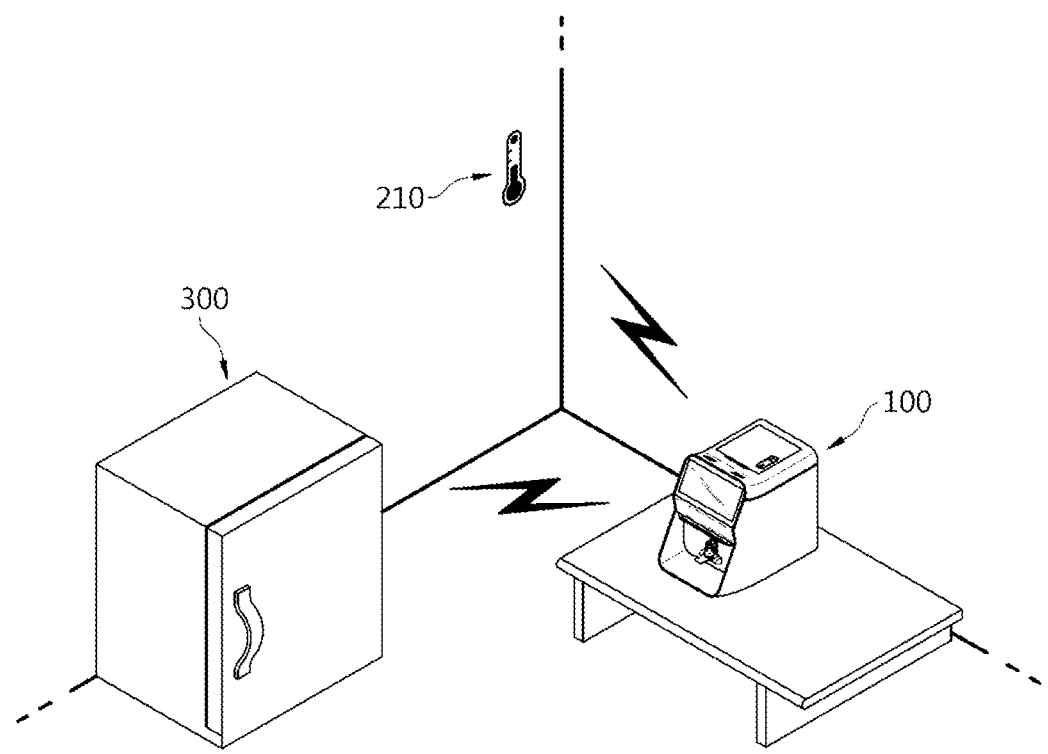
FIG. 6 is a diagram illustrating a room in which a test apparatus is located according to an exemplary embodiment.
Figure 7:
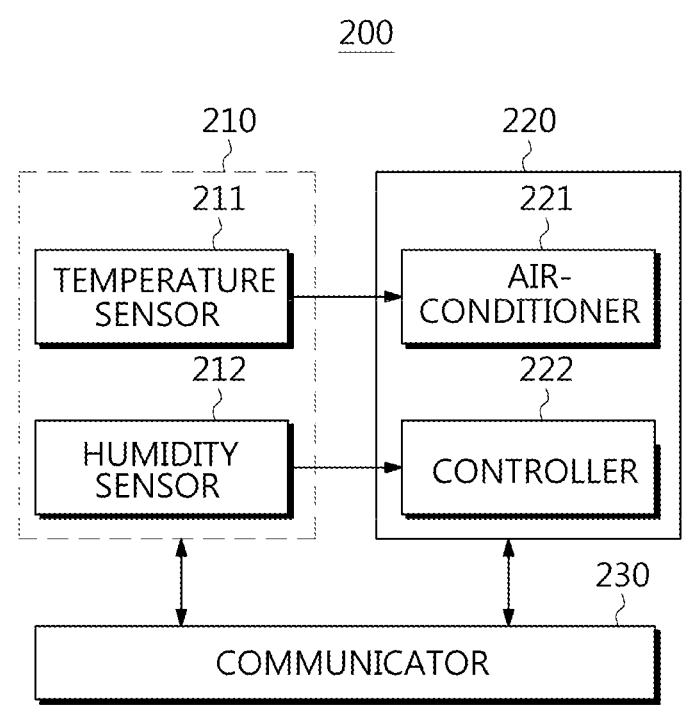
FIG. 7 is a block diagram illustrating an external air-conditioner according to an exemplary embodiment.
Figure 8:
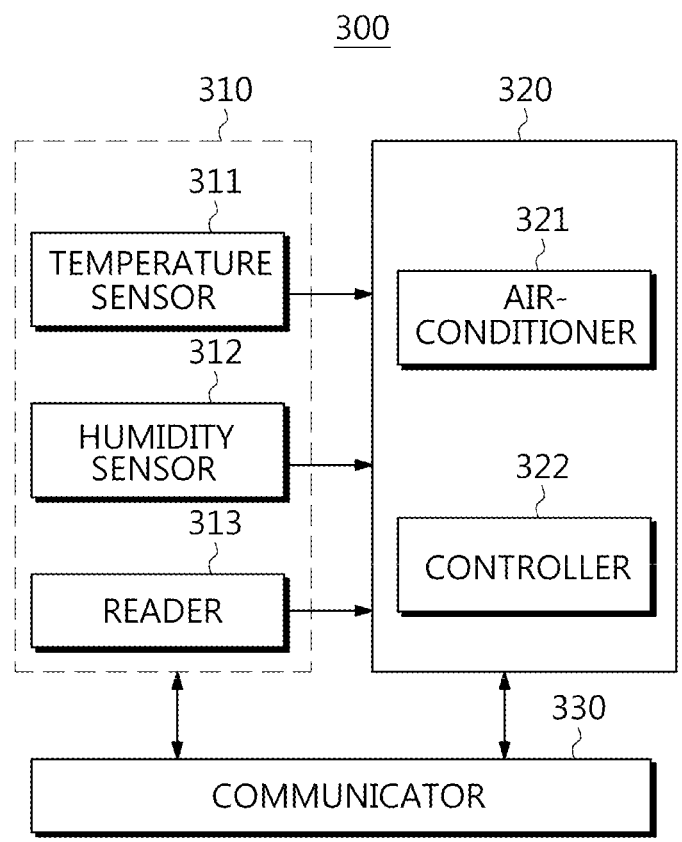
FIG. 8 is a block diagram illustrating a storage according to an exemplary embodiment.

FIG. 6 is a diagram illustrating a room in which a test apparatus is located according to an exemplary embodiment. FIG. 7 is a block diagram illustrating an external air-conditioner according to an exemplary embodiment. FIG. 8 is a block diagram illustrating a storage according to an exemplary embodiment. For convenience of description, the test apparatus 100 in which the cartridge-type reaction device 10 is inserted is described as an example.

Referring to FIG. 6, the test apparatus 100, the external sensor 210, and the storage 300 may be located in the same room. The external sensor 210 may detect at least one of a temperature and humidity of the room, and may transmit the detected one to the test apparatus 100.

Because the external sensor 210 and the test apparatus 100 are located in the same room, the temperature and humidity sensed by the external sensor 210 may be an external temperature and an external humidity, respectively. Although the testing of the reagent contained in the reaction device 10 is performed in the test apparatus 100, the external temperature or humidity may affect the control of the internal temperature or humidity of the test apparatus 100. Therefore, the external temperature or humidity of the test apparatus 100 may also be important control parameters.

In addition, because the storage 300 is located in the same room as the test apparatus 100, the environment of the reaction device 10 released from the storage 300 can be estimated based on the temperature and humidity detected by the external sensor 210. For example, the environment of the reaction device 10 may also be used as an important parameter for various control actions performed by the test apparatus 100.

Although FIG. 6 exemplarily shows that the external sensor 210, the test apparatus 100, and the storage 300 are located in one room, the exemplary embodiments are not limited thereto. Accordingly, it should be noted that the storage 300 may also be located in another room different from that of the test apparatus 100. In addition, if the storage 300 is located in a different room than the test apparatus 100, an external sensor 210 located in the same room as the storage 300 may further be provided.

In addition, although FIG. 6 exemplarily illustrates that one test apparatus 100 communicates with one external sensor 210 and one storage 300, the exemplary embodiments are not limited thereto. As another example, a plurality of test apparatuses 100 may communicate with the external sensor 210 and the storage 300, or a plurality of storages 300 may communicate with the test apparatus 100.

As described above, an example in which a plurality of devices communicate with each other to share information therebetween may be referred to as an Internet of Things (IoT).

Although FIG. 6 exemplarily shows only the external sensor 210, it should be noted that the air-conditioner adjusting the external environment may be connected to the test apparatus 100 so that the test apparatus 100 may directly control the external environment, an example of which is described with reference to FIG. 7.

Referring to FIG. 7, air-conditioner apparatus 200 includes an external sensor 210, an air-conditioner unit 220, and a communicator 230.

The external sensor 210 may include a temperature sensor 211 for sensing temperature and a humidity sensor 212 for sensing humidity. As another example, the external sensor 210 may include only the temperature sensor 211 or the humidity sensor 212. In this case, the term "external sensor" is based on the test apparatus 100.

The air-conditioner unit 220 includes an air-conditioner 221 that may cool, heat, or otherwise purify suctioned air using a transfer of heat generated in the evaporating and condensing process of refrigerant, and may discharge the cooled, heated or purified air, so that air-conditioning (e.g., cooling, heating, dehumidifying) of the air included in a room or space may be performed.

The air-conditioner unit 220 also includes a controller 222 that may control the air-conditioner 221 according to the temperature or humidity information that is sensed by the temperature sensor 211 or the humidity sensor 212, according to a control command of a user or a control signal of the test apparatus 100 received from the communicator 230. Accordingly, the controller 222 may control the air in the room so that the temperature or humidity of the room including the test apparatus 100, i.e., the external temperature or humidity of the test apparatus 100, can be adjusted.

The communicator 230 may include at least one of a Bluetooth communication module for communicating with a single external device on a one-to-one basis or for communicating with a small number of external devices on a one-to-multiple basis, a Wireless Fidelity (Wi-Fi) communication module for connection to a local area network (LAN) through an access point (AP) or the like, and a near field communication (NFC) module, such as a ZigBee communication module, for forming a local area network (LAN) between the test apparatus 100 and the communication unit 230.

However, although the communication module contained in the communication unit 230 may be at least one of a Bluetooth communication module, a Wi-Fi communication module, and a near field communication (NFC) module, the exemplary embodiments are not limited thereto, and the communication module may also include other communication modules that are capable of communicating with the communicator 110 of the test apparatus 100.

Referring to FIG. 8, the storage 300 includes a sensing unit 310 for sensing the internal environment of the storage and a reaction device stored in the storage, an air-conditioner unit 320 for controlling the internal temperature or humidity of the storage 300, and a communicator 330 for communicating with the test apparatus 100.

The sensing unit 310 may include a temperature sensor 311 for sensing the internal temperature of the storage 300, a humidity sensor 312 for sensing humidity of the storage 300, and a reader 313 for reading a tag attached to the reaction device.

The tag may include unique information related to the corresponding reaction device and may be provided in the reaction device. For example, the tag may be attached to the surface of the reaction device. As a non-limiting example, the tag may be at least one of a barcode, a two-dimensional (2D) code such as a QR code, an RFID tag, an NFC tag, a Bluetooth tag, and the like. Therefore, the reader 313 may include at least one of an image sensor for capturing a two-dimensional (2D) code, an RFID reader for reading the RFID tag, an NFC reader for reading the NFC tag, and a Bluetooth reader for reading the Bluetooth tag.

Unique information that is contained in the tag may include identification (ID) information such as a serial number, a production lot number, test process information applied to the corresponding reaction device, information regarding a reagent accommodated in the corresponding reaction device, information regarding a sample that is to be inserted into the corresponding reaction device, information about a production day of the sample, information about a manufacturing facility, and the like. However, the unique information contained in the tag is not limited to the above information, and may not always include all of the above information. Also, the unique information may include other information other than the above information, or may also include only some parts of the above information. In the examples herein, information contained in the tag will be referred to as reaction device information.

On the other hand, the reaction device information may be acquired not only using the tag and the reader but also using other schemes. For example, the user may input the reaction device information, the reaction device information may be transmitted from other devices such as a storage, and the like.

The communicator 330 may include at least one of a Bluetooth communication module for communication with a single external device on a one-to-one basis or for communicating with a small number of external devices on a one-to-multiple basis, a Wireless Fidelity (Wi-Fi) communication module for connecting to a local area network (LAN) through an access point (AP) or the like, and a near field communication (NFC) module, such as a ZigBee communication module, for forming a local area network (LAN) between the test apparatus 100 and the communicator 330.

However, although the communication module contained in the communicator 330 may be any one of a Bluetooth communication module, a WiFi communication module, and a near field communication (NFC) module, the scope or spirit of the exemplary embodiments are not limited thereto, and the communication module may also include other communication modules that are capable of communicating with the communicator 110 of the test apparatus 100.

The air-conditioner unit 320 includes an air-conditioner 321 that may cool, heat, or otherwise purify suctioned air using a transfer of heat generated in the evaporating and condensing process of refrigerant, and may discharge the cooled, heated or purified air, so that air-conditioning (e.g., cooling, heating, dehumidifying) of the storage 300 may be performed.

The air-conditioner unit 320 also includes a controller 322 that may control the air-conditioner 321 according to the temperature or humidity information that is sensed by the temperature sensor 311 or the humidity sensor 312, according to a control command of a user or a control signal of the test apparatus 100 received from the communicator 330. Accordingly, the controller 322 may control the air in the room so that the temperature or humidity of the room including the test apparatus 100, i.e., the external temperature or humidity of the test apparatus 100, can be adjusted.

Figure 9:
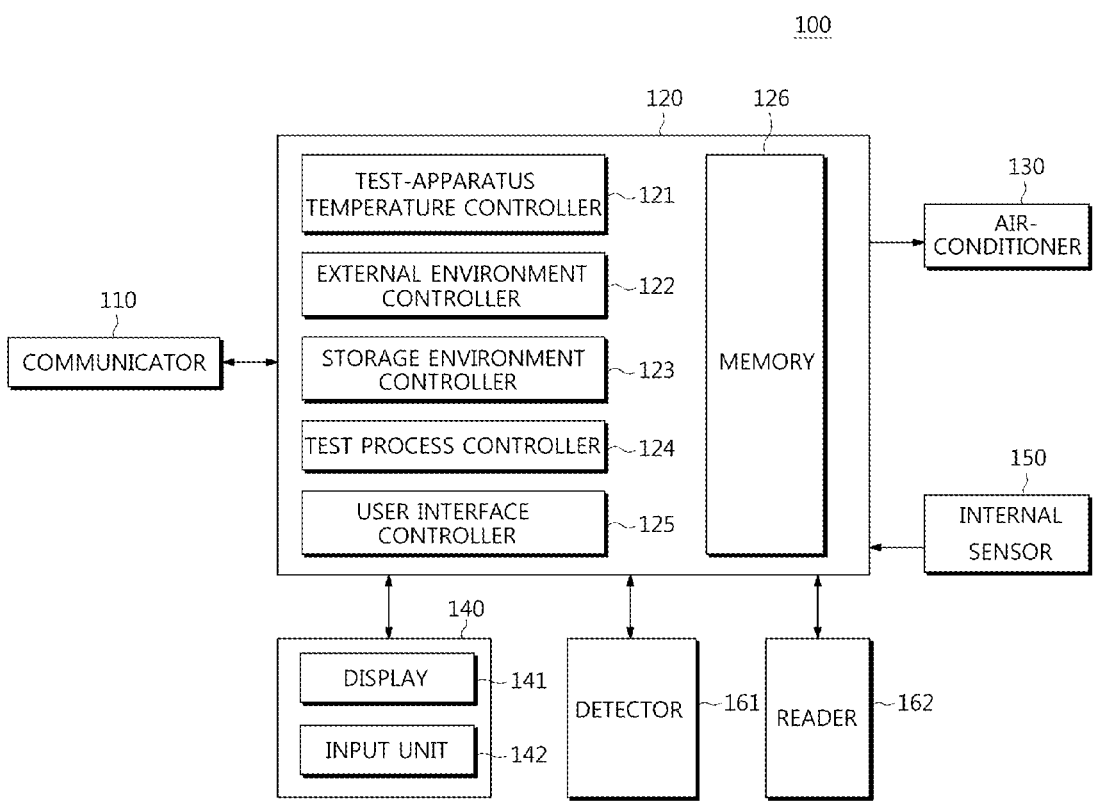
FIG. 9 is a block diagram illustrating a test apparatus according to another exemplary embodiment.

FIG. 9 is a block diagram illustrating a test apparatus according to another exemplary embodiment.

Referring to FIG. 9, the controller 120 includes a test-apparatus temperature controller 121 for controlling the internal environment of the test apparatus 100, an external environment controller 122 for controlling the external environment of the test apparatus 100, a storage environment controller 123 for controlling the environment of the storage 300, a test process controller 124 for controlling a test process when the reaction device is inserted in such a manner that a test appropriate for the inserted reaction device can be performed, a user interface controller 125 for controlling a user interface, and a memory 126.

The test-apparatus temperature controller 121, the external environment controller 122, the storage environment controller 123, the test process controller 124, or the user interface controller 125 may be implemented as an independent or separate processor, and two or more controllers may share one processor.

The test apparatus 100 may include an air-conditioner 130 for adjusting an internal temperature or humidity, and may heat or cool the internal air of the test apparatus 100 according to a testing category or a testing process. Also, the air-conditioner 130 may perform dehumidification in such a manner that the internal humidity of the test apparatus 100 can be adjusted according to test conditions.

The test apparatus 100 may include a user interface 140 including a display 141 for providing a variety of information to a user, and an input unit 142 configured to receive a control command from the user.

The display 141 may be implemented as or include at least one of various display devices, for example, a Light Emitting Diode (LED), an Organic Light Emitting Diode (OLED), a Liquid Crystal Display (LCD), a Plasma Display Panel (PDP), a Cathode Ray Tube (CRT), and the like.

The input unit 142 may be implemented as or include a hard key or a touch panel. For example, a touch panel may be mounted to the front surface of the display 141 so that a touchscreen is implemented and a power button may be implemented as a hard key. Therefore, after the test apparatus 100 is powered on, the user may contact the touchscreen so that the user can input a control command.

The test apparatus 100 may include an internal sensor 150 for sensing temperature or humidity. When the internal temperature or humidity of the test apparatus 100 is controlled, information generated from the internal sensor 150 may be used along with information received from the communicator 110.

The test apparatus 100 may further include a detector 161 for detecting a reaction generated in the inserted reaction device, and a reader 162 for reading the tag mounted to the reaction device to recognize the inserted reaction device.

For example, if a reaction generated in the reaction device is a response for changing optical characteristics of a material, the detector 161 may include a light source and a light receiving element. For example, the light source may emit light having a specific wavelength to the chamber 12*a* formed in the reaction device 10, and the light receiving element may receive the light having passed through the chamber 12*a* or receive the light reflected from the chamber 12*a*, so that a reaction can be detected.

An example description of the reader 162 is the same as that of the reader 313 of the storage 300. Therefore, the construction of the reader 162 may be changed according to categories of the tag formed in the reaction device 10. Meanwhile, if the tag formed in the reaction device 10 is a 2D barcode, the light receiving element of the detector 161 may be used as the reader 162. That is, the detector 161 and the reader 162 may wholly or partially overlap with each other.

Examples of information indicating what information is communicated among the test apparatus 100, the external air-conditioner 200, and the storage 300, and examples of information indicating which control is applied to the test apparatus 100 according to reception information are hereinafter described with reference to the following exemplary embodiments.

FIGS. 10 to 13 are screen images illustrating a process for registering an external temperature sensor with the test apparatus, and a process for registering an external air-conditioner or registering a storage connection with the test apparatus, according to various exemplary embodiments.

Figure 10:
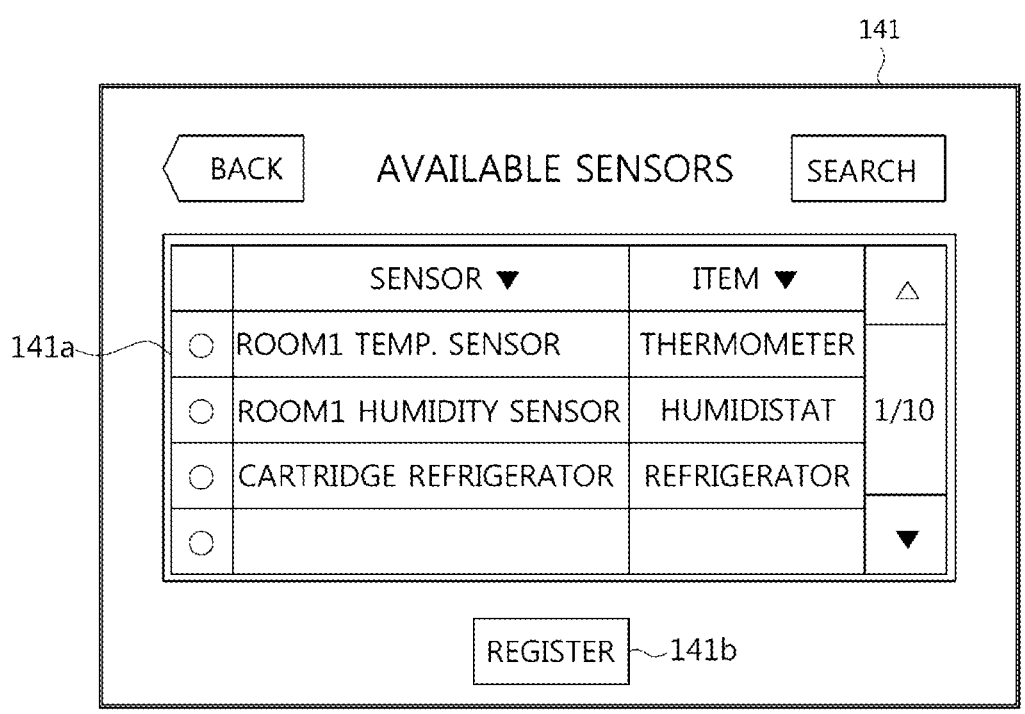
FIGS. 10 to 13 are screen images illustrating a process for registering an external temperature sensor with a test apparatus, and a process for registering an external air-conditioner or registering a storage connection with the test apparatus according to various exemplary embodiments.

Referring to FIG. 10, a screen image may be displayed on the display 141 of the test apparatus 100. For example, the screen image may be connected to the test apparatus 100 over a network so that the user can select a target object for signal transmission/reception using the screen image. In response, a list 141*a* of sensors or storages including a module that is located at a specific position at which communication with the test apparatus 100 is possible and is capable of communicating with the test apparatus 100 may be displayed. Accordingly, the user may select a desired sensor or storage to be connected, select a registration button 141*b*, and connect a desired sensor or storage to the test apparatus 100. As described above, if the display 141 and the input unit 142 construct the touchscreen, the user may select the desired sensor or storage by touching a desired button of the display screen image.

Figure 11:
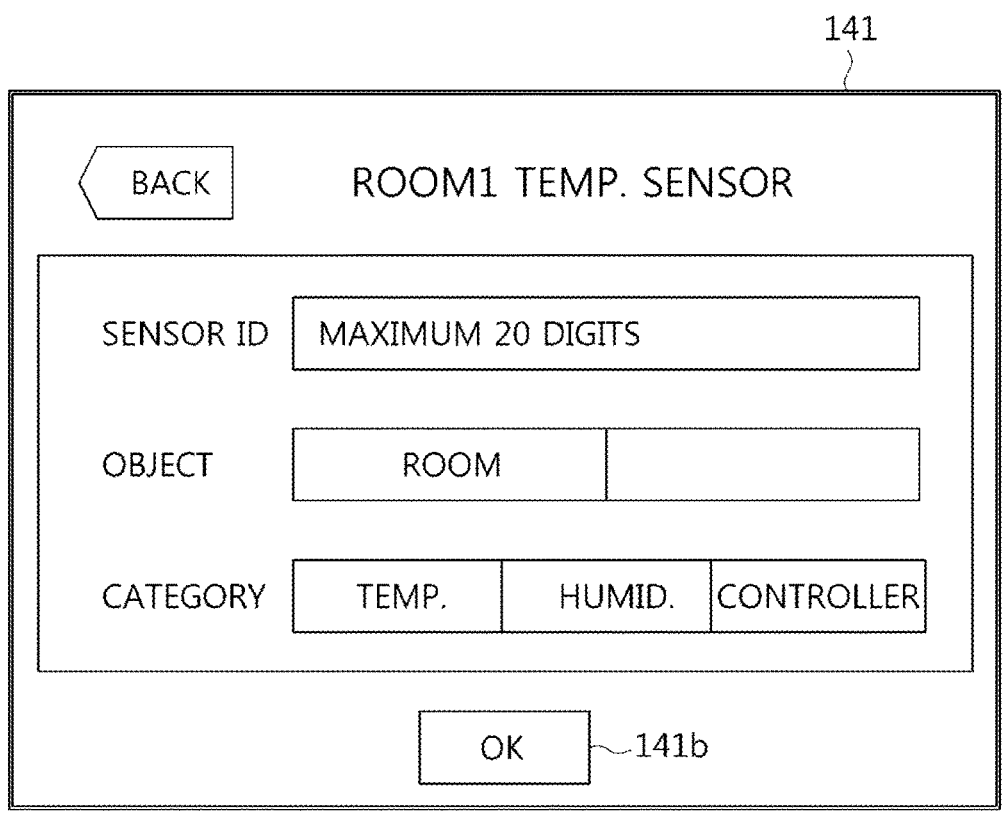
Figure 12:
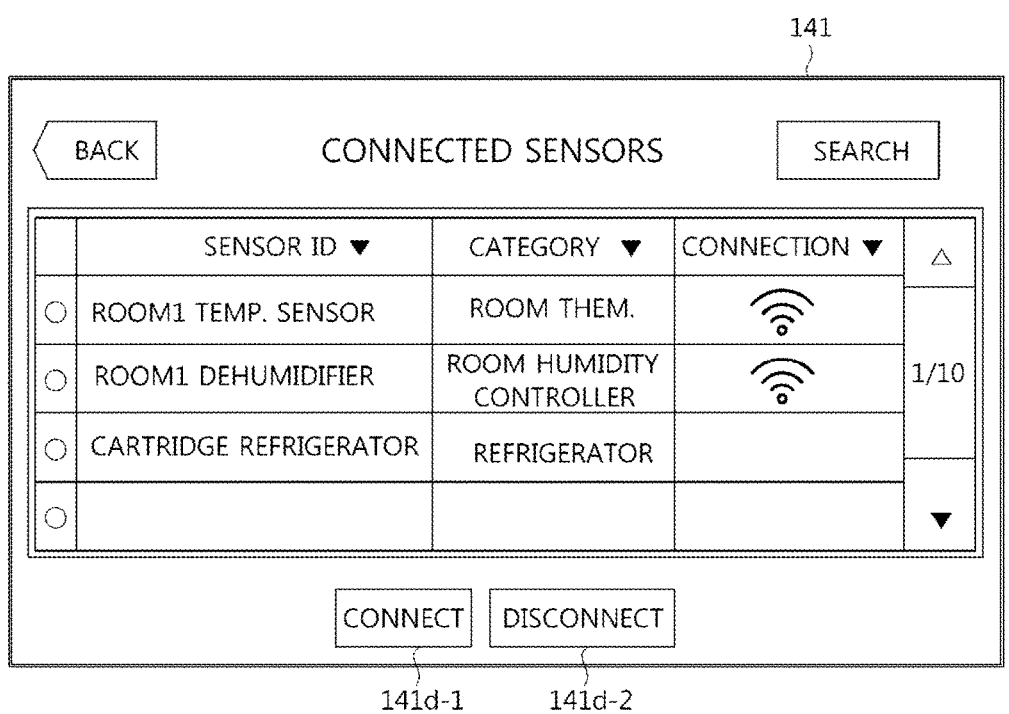

For example, a desired device is selected from the screen image shown in FIG. 10 (i.e., "Room1 temperature sensor" is selected). Accordingly, an ID for identifying the selected device is registered as shown in FIG. 11, and the user may input the use purpose and category information of the selected device. If information is input and the OK button 141 is selected, the corresponding device is registered to be connected to the test apparatus 100 as shown in FIG. 12. In this example, all or some parts of the registered devices may be selected, and the "Disconnect" button 141*d*-2 may be selected to release the device from the test apparatus 100, or the "Connect" button 141*d*-1 may be selected so that the device is reconnected to the test apparatus 100. That is, other devices connectable to the test apparatus 100 may be freely connected or released using the user interface 140 provided by the test apparatus 100.

Figure 13:
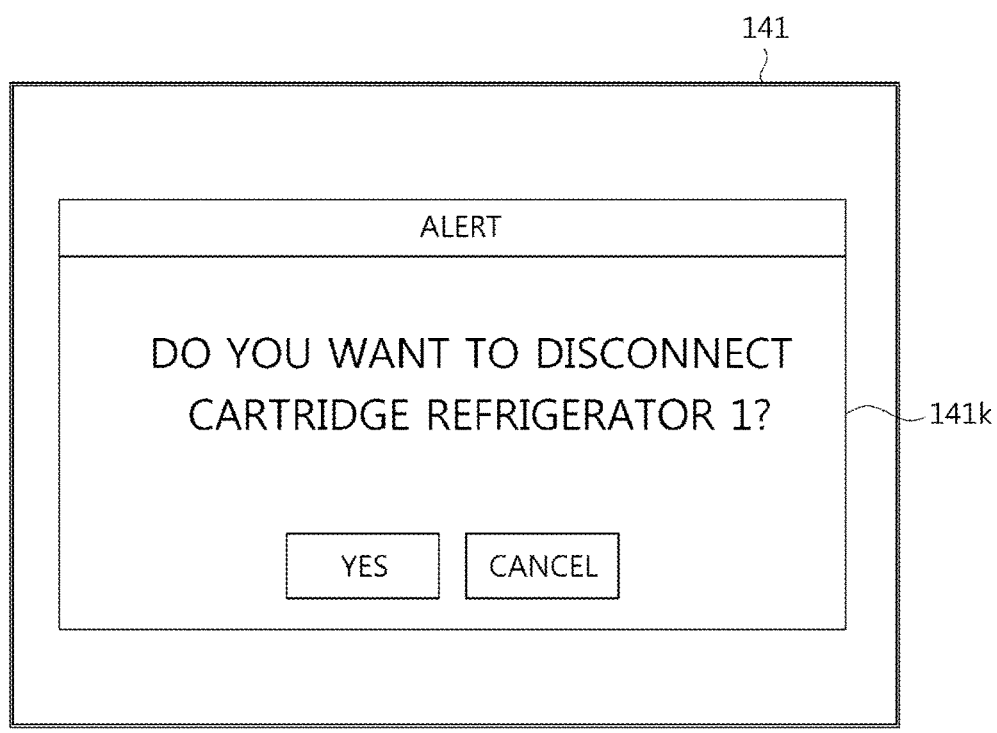

In addition, if the external air-conditioner 200 or the storage 300 is replaced, an alarm screen image 141*k* for indicating a potential connection release may be displayed on the display unit 141 as shown in FIG. 13.

For example, the user interface controller 125 may control the user interface 140 at a specific point in time at which information should be provided to the user or the user should input information, and the screen image as shown in FIGS. 10 to 13 may be displayed.

The screen images shown in FIGS. 10 to 13 are examples of the screen that are capable of being displayed on the test apparatus 100, however, exemplary embodiments of the test apparatus 100 are not limited to the above-mentioned exemplary screen images. In addition to the screen images, other content or other screen constructions may be applied, and information may be provided to the user or an input signal for the user may be derived.

While the devices connected to the test apparatus 100 are powered on, information or signals for communication with the test apparatus 100 can be transmitted and received. Signals may be transmitted and received, or may be periodically transmitted/received when a specific event occurs. In addition, the number of transmission/reception (Tx/Rx) actions or the Tx/Rx time may be changed according to contents of Tx/Rx signals.

For example, if the test apparatus 100 is powered on, the test apparatus 100 may receive the external environment information from the external sensor 210. In this example, the external environment information may include the temperature and humidity information of the space in which the test apparatus 100 is located. The test-device environment controller 110 may transmit a control signal to the internal air-conditioner 130 to preheat the main body 107, prior to starting a first test based on the received temperature and humidity information.

Figure 14:
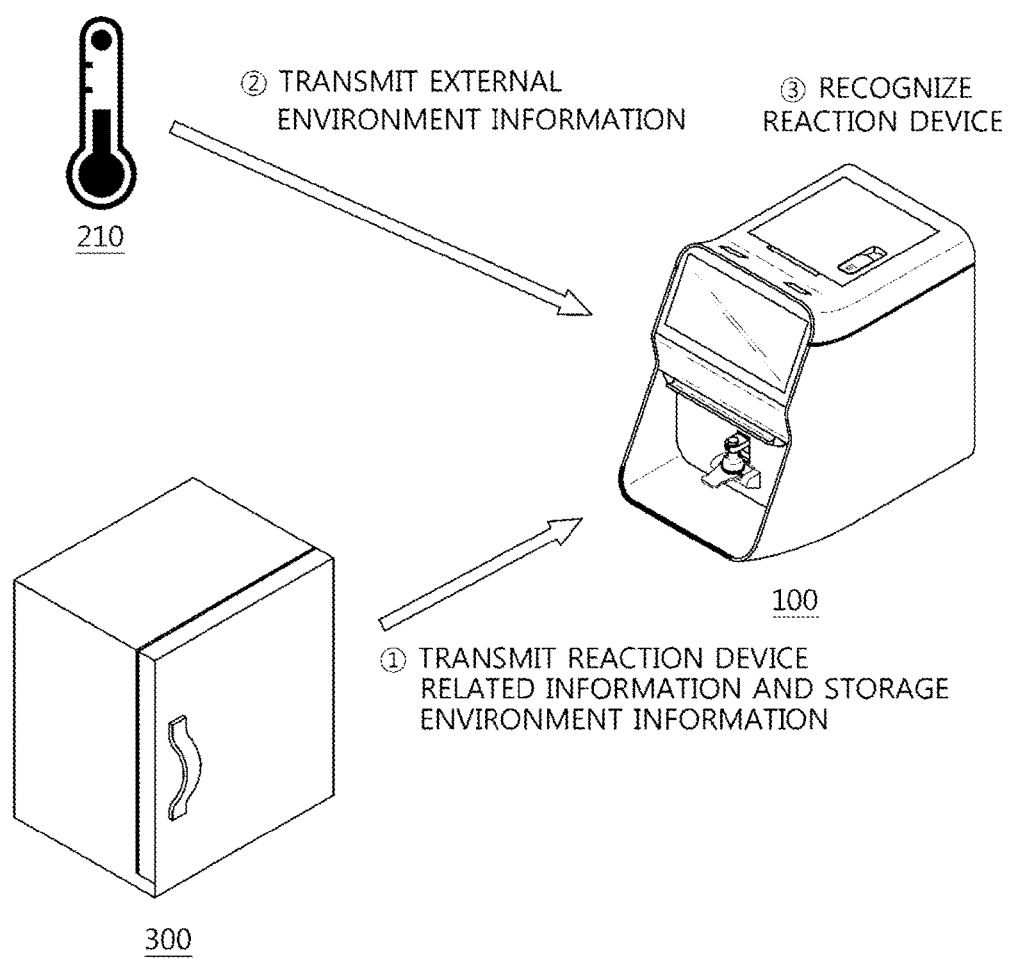
FIGS. 14 to 16 illustrate examples of the test apparatus being controlled base on information received from a storage and an external sensor according to various exemplary embodiments.
Figure 15:
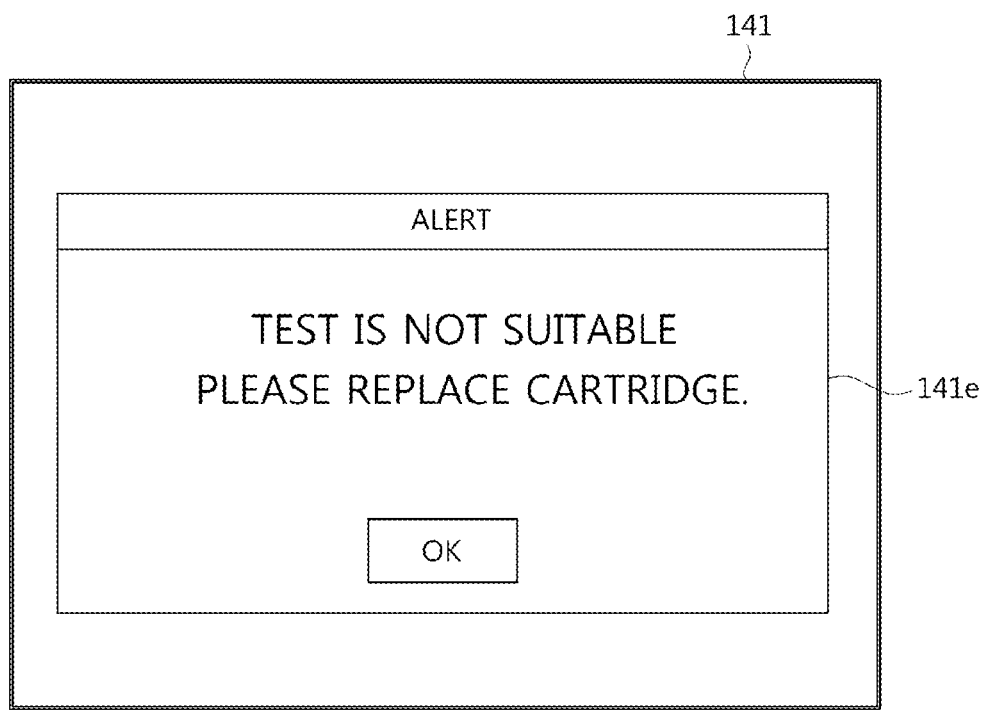
Figure 16:
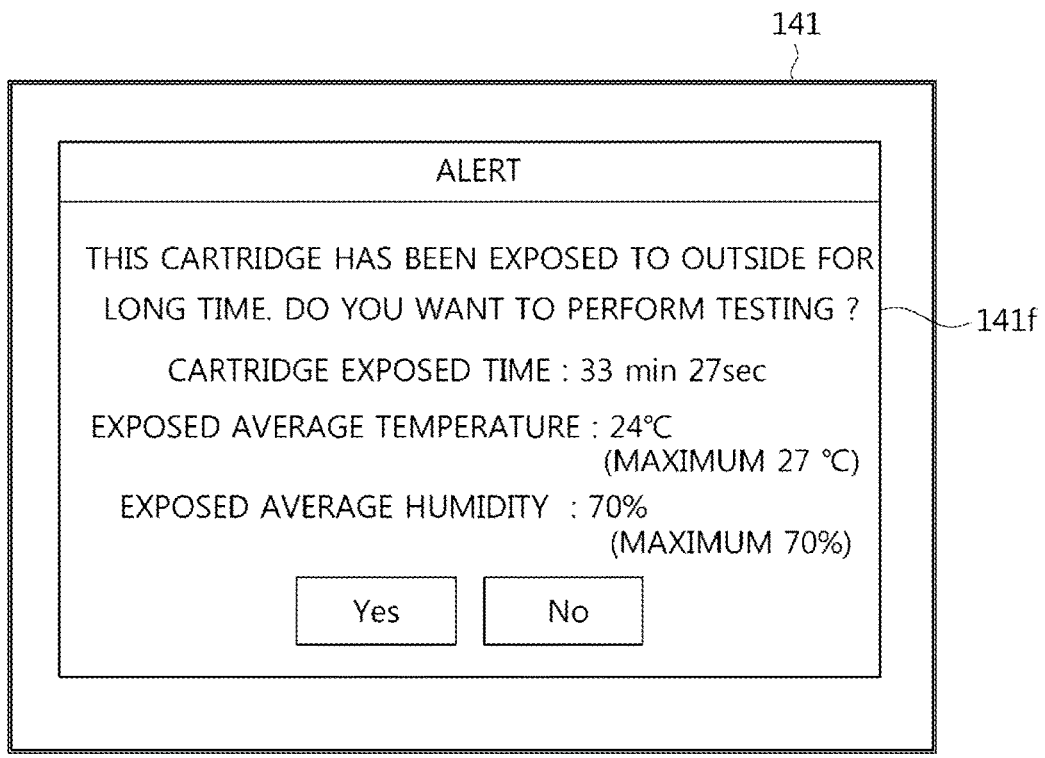

FIGS. 14 to 16 illustrate examples of the test apparatus being controlled based on information received from the storage and the external sensor according to various exemplary embodiments.

The reader 313 of the storage 300 reads the tag contained in the reaction device 10, and the test apparatus 100 can obtain information about the entry time and the exit time of each reaction device 10. For example, the entry time and/or the exit time of the reaction device 10 may be referred to as storage time information.

As shown in FIG. 14, the communicator 330 of the storage 300 may transmit reaction device-related information and storage environment information to the communicator 110 of the test apparatus 100. For example, the reaction device-related information may include reaction device information obtained by reading the tag of the reaction device 10, and information about the entry/exit time of the reaction device 10. Also, the storage environment information may be obtained from the temperature sensor 311 and the humidity sensor 312. If the test apparatus 100 requests the above-mentioned information, this information may be transmitted or may be periodically transmitted. As another example, this information may be transmitted when the reaction device 10 is loaded or unloaded.

The external sensor 210 may transmit information about the external temperature and humidity to the communicator 110 of the test apparatus 100. If the test apparatus 100 requests information about the external temperature and humidity, the external sensor 210 may transmit the requested information, or may periodically transmit the requested information in real time. In addition, it is possible to transmit the temperature and humidity data for a predetermined time range based on a transmission (Tx) time at which data is transmitted to the test apparatus 100. Also, temperature and humidity information may be transmitted at a specific time.

The test apparatus 100 may temporarily, semi-permanently, or permanently store the received information in the memory 126. If the reaction device 10 is inserted into the reaction device 100, the reaction device 152 may recognize the reaction device 10. For example, the reader 162 may read the tag mounted to the reaction device 10, and the reader 162 may obtain the reaction device information contained in the tag.

The test process controller 124 of the test apparatus 100 may determine whether a current external environment is appropriate for test execution based on the external temperature and humidity information. For example, if at least one of the external temperature and the external humidity exceeds a reference range appropriate for testing, the test process controller 124 may prevent the test from being executed, and may inform a user that a current external environment is unsuitable for testing.

Alternatively, if only one of the internal temperature and humidity of the test apparatus 100 exceeds a reference range appropriate for the testing, the test process controller 124 may prevent the test from being executed, and may inform a user of a current internal environment and why it is unsuitable for testing.

The test process controller 124 may compare the reaction device information obtained by reading the tag of the inserted reaction device 10 with the reaction device-related information stored in the memory 126, so that the test process controller 124 may determine information related to the currently inserted reaction device 10. For example, the test process controller 124 may compare a first time at which the inserted reaction device 10 exits the storage 300 with a second time at which the reaction device 10 is inserted into the test apparatus 100, and the test process controller 124 can recognize how long the reaction device 10 is exposed to the outside by comparing the times. In addition, the test process controller 124 may determine the external environment in which the reaction device is exposed to the outside, upon receiving the external temperature and humidity information, and may determine which environment is used to store the storage 300 based on the storage environment information. In addition, at least one of a current temperature and a current humidity of the reaction device 10 can be estimated based on the above-mentioned determination results.

For example, if the reaction device 10 is stored at a temperature or humidity inappropriate for the storage 300, or if at least one of the estimated temperature and humidity of the reaction device exceeds a reference range appropriate for testing, a warning screen image 141e including a message for instructing the user to replace the reaction device because it is not suitable to perform testing may be displayed on the display unit 141 as shown in FIG. 15. Information regarding the recommended storage environment is contained in the reaction device information. If the storage state of the storage unit 300 is inappropriate for the recommended storage environment of the reaction device, this means that the temperature or humidity of the storage unit 300 is inappropriate. For example, whether the recommended storage environment matches a storage state of the storage may be determined.

Generally, the storage 300 may store the sample or reagent at a low temperature, for example, a temperature of about 5° C. Therefore, before the test is executed by inserting the reaction device into the test apparatus 100, the reaction device may be exposed to the outside at room temperature for a predetermined amount of time. For example, a recommended standing time of ten minutes may be suggested. If the reaction device is exposed to the outside at room temperature for longer than 10 minutes and is then inserted, the warning screen image 141f may display a message. For example, the warning screen image may include not only a message indicating that the reaction device was exposed to the outside at a room temperature for a long period of time, but also information about the exposed time, the average temperature during exposure, and the average humidity of the exposed reaction device may be displayed on the display 141 as shown in FIG. 16. Even when the reaction device is exposed to the outside at room temperature for a long period of time, a temperature of the reaction device may be appropriately maintained so that no problems will occur during testing. Therefore, the user may confirm the warning screen image 141*f* displayed on the display unit 141, and may determine whether testing should be carried out.

In an example in which the inserted reaction device is not exposed to the outside for a long period of time, the estimated temperature of the reaction device may not exceed the reference temperature range or reference humidity range. Accordingly, and the external environment is appropriate for testing and testing may be performed. The test process controller 124 may perform testing according to an appropriate process for the inserted reaction device, and the process may be obtained from the tag included in the reaction device.

For such testing, the internal environment of the test apparatus 100 may be appropriately controlled to prevent inaccurate results. For example, the test-apparatus temperature controller 121 may control the internal environment of the test apparatus 100 based on the estimated temperature or humidity of the reaction device, and/or the internal temperature or humidity (of the test apparatus 100) sensed by the internal sensor 150. As described above, the temperature or humidity of the reaction device may be estimated based on a variety of information, for example, the entry/exit time to/from the storage 300, the storage temperature in the unit 300, the standing time, the external environment, and the like, so that the above information may be correctly estimated and the test apparatus 100 may be accurately controlled based on the estimation result. For example, the reaction device exiting from the storage 300 may not be exposed to the outside at room temperature, and the test apparatus 100 may also be immediately inserted.

Figure 17:
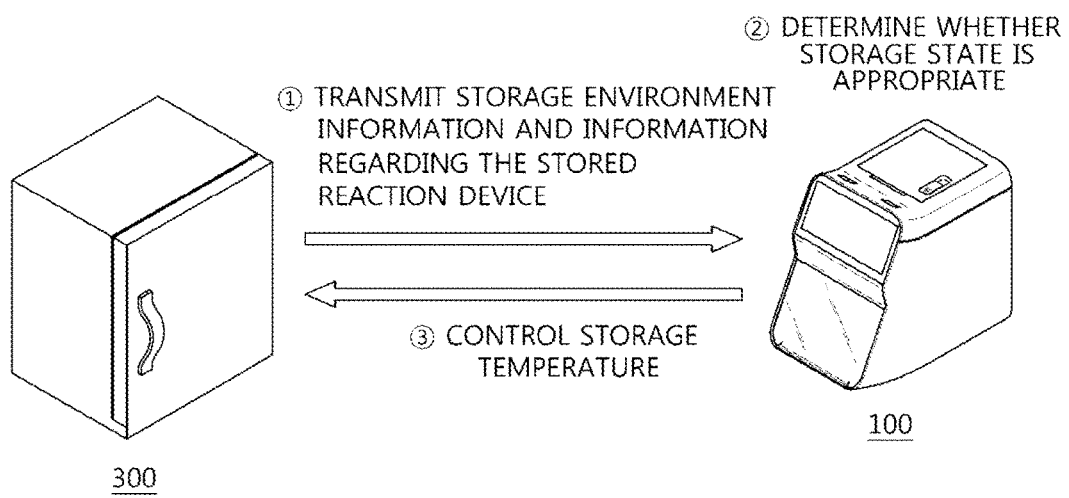
FIGS. 17 and 18 are diagrams illustrating examples for controlling a temperature of a storage using the test apparatus according to various exemplary embodiments.
Figure 18:
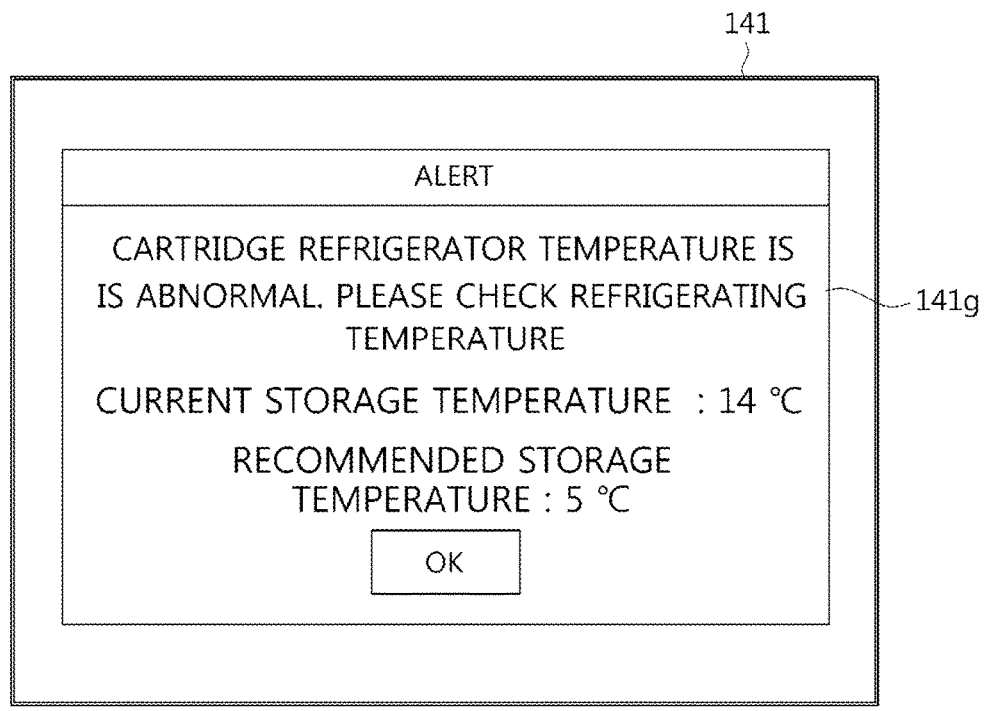

FIGS. 17 and 18 are diagrams illustrating examples for controlling a temperature of a storage using the test apparatus according to various exemplary embodiments.

Referring to FIG. 17, even while the reaction device is not inserted into the test apparatus 100, the storage 300 may periodically transmit storage environment information and information about the stored reaction device to the test apparatus 100. The storage environment controller 123 of the test apparatus 100 may compare the recommended storage temperature and humidity that are contained in the reaction device information with an internal temperature and a humidity of the storage 300 contained in the storage environment information, and determine whether the storage state of the storage 300 is appropriate or inappropriate.

If the current storage environment is determined to be inappropriate to store the reaction device, and if the test apparatus 100 can directly control the temperature or humidity of the storage 300, a control signal may be applied to the storage 300, so that at least one of the temperature and the humidity may be controlled to an appropriate level.

Alternatively, as can be seen in the example of FIG. 18, a warning screen image 141*g* including a message indicating that a storage temperature is abnormal, and also indicating the current storage temperature and the recommended storage temperature may be displayed on the display 141, so that a user may directly control the temperature of the storage unit 300.

As another example, the storage 300 may determine whether or not the storage environment is appropriate. For example, information may be transmitted to the test apparatus when the storage environment is inappropriate for storing the reaction device.

Figure 19:
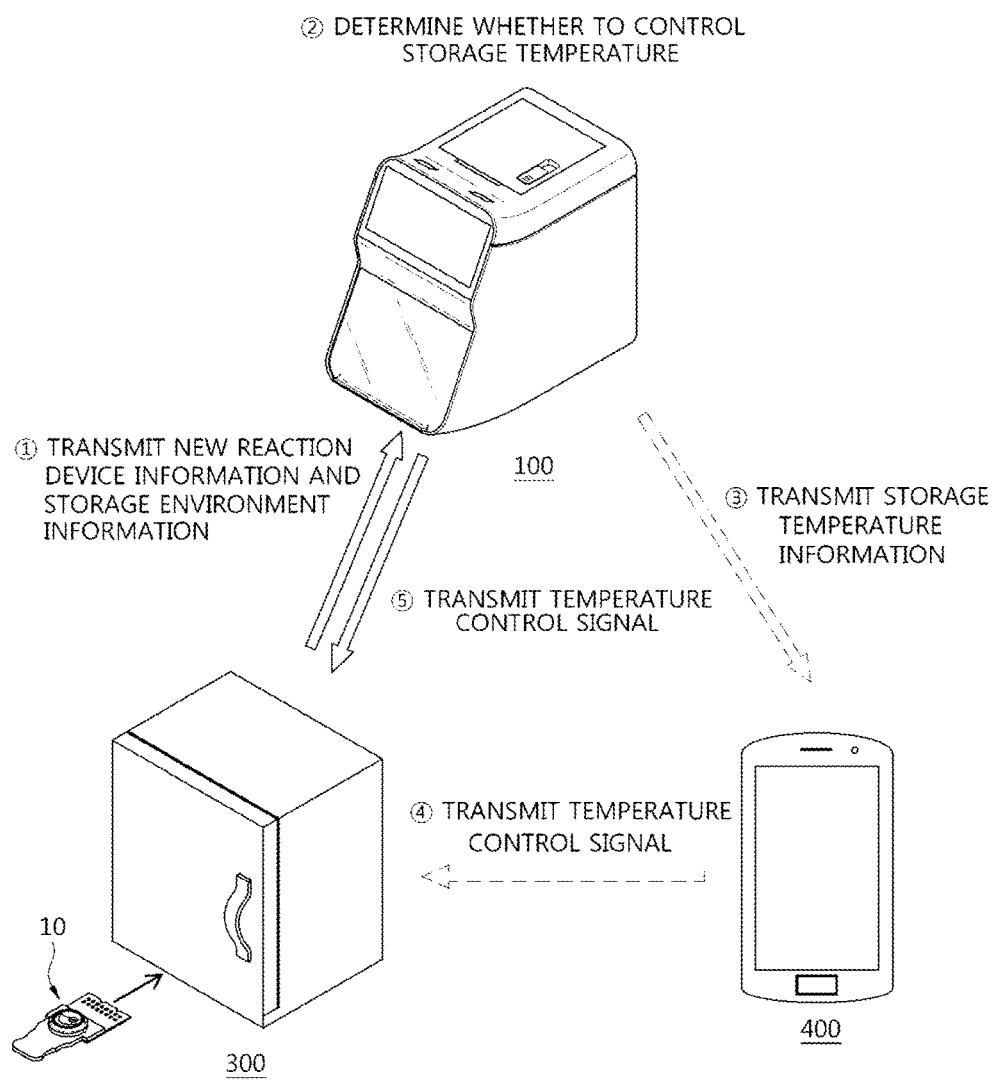
FIG. 19 is a diagram illustrating a method for controlling a temperature of a storage using a test apparatus when a new reaction device is added according to an exemplary embodiment.

FIG. 19 is a diagram illustrating an example of controlling a temperature of a storage using a test apparatus when a new reaction device is added according to an exemplary embodiment.

Referring to FIG. 19, when a new reaction device 10 is inserted into the storage 300, the reaction device information and the storage environment information may be transmitted to the test apparatus 100. For example, the storage environment controller 124 of the test apparatus 100 may compare the recommended storage temperature included in the reaction device information with a storage temperature included in the storage environment information, and may determine whether or not the temperature is appropriate.

In this example, the test apparatus 100 may directly control a temperature of the storage 300, transmit information to the mobile device 400 of the user, and thus, request direct control of the user. As another example, the user may control the test apparatus 100 through the mobile device 400. For example, the mobile device 400 may be pre-registered through an application so that the mobile device 400 may communicate with the test apparatus 100 or the storage 300.

For example, the test apparatus 100 may transmit storage temperature information to the pre-registered mobile device 400, and the mobile device 400 may display the corresponding information on the screen. In this example, the user may confirm the corresponding information so that the user may directly control a temperature of the storage 300 based on the confirmed information, and may transmit a temperature control signal to the storage 300 through the mobile device 400.

If a user is unable to control a temperature of the storage 300 even though storage temperature information is transmitted to the mobile device 400, the storage environment controller 123 of the test apparatus 100 may transmit a temperature control signal to the storage 300, and may adjust a temperature of the storage 300 according to a storage temperature of the new reaction device 10.

In addition, as can be seen from FIG. 18, the test apparatus 100 may transmit storage temperature information to the mobile device 400, so that the user may directly control a temperature of the storage 300, or may control a temperature of the storage 300 through the mobile device 400.

Although temperature control of the storage is shown in the examples of FIGS. 17 to 19, it should be noted that the above-mentioned storage control may also be applied to humidity without departing from the exemplary embodiments.

Figure 20:
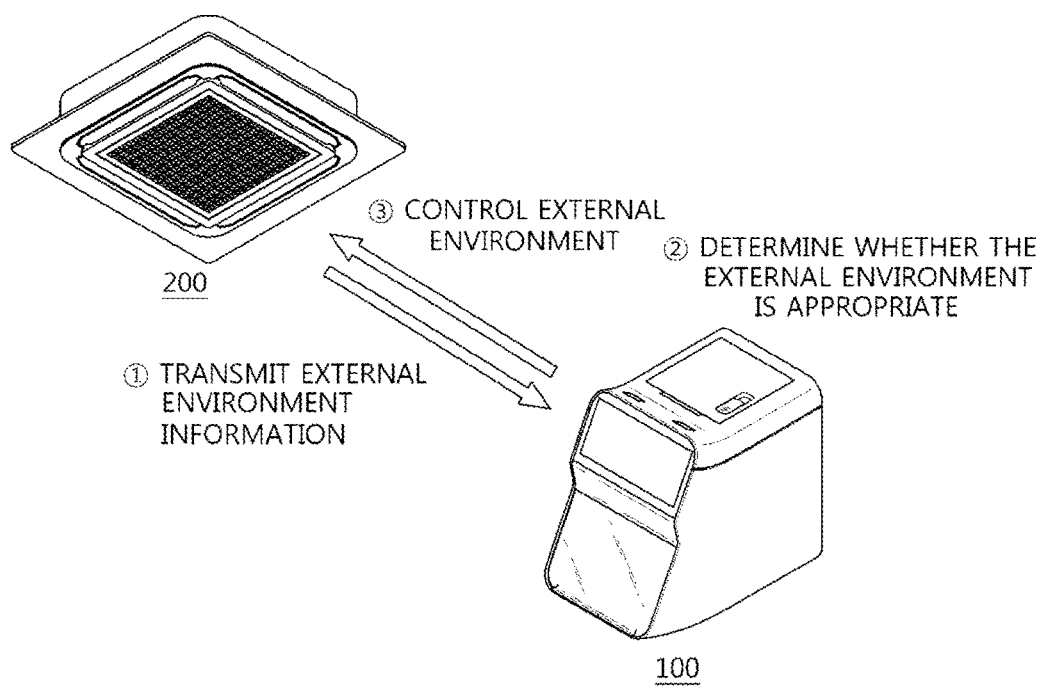
FIG. 20 is a diagram illustrating a method for controlling an external environment using a test apparatus according to an exemplary embodiment.

FIG. 20 is a diagram illustrating an example of controlling the external environment using a test apparatus according to an exemplary embodiment.

Referring to FIG. 20, when testing is completed, or if a standby state for waiting for such testing is given, the test apparatus 100 may allow the external environment to be appropriately maintained for testing. For example, upon receiving the external environment information including at least one of the external temperature and the humidity from the air-conditioner 200, the external environment controller 122 may determine whether the external environment is suitable for testing.

For example, a reference range for the external temperature or a humidity appropriate for the standby state may be pre-configured. If the transmitted external temperature or humidity information exceeds a predetermined reference range for either, a message indicating that the testing environment is unsuitable may be displayed on the display 141 to prevent such testing, or the test apparatus 100 may transmit a control signal to the air-conditioner 200 so that the external environment can be directly and automatically controlled. If external environment control failure occurs, the external environment information and a message indicating external environment control failure may be transmitted to the pre-registered mobile device. Accordingly, a user of the mobile device can recognize the external environment information and the control failure state.

Meanwhile, it may be possible to control the internal temperature or humidity of the test apparatus 100 in a standby state based on the external environment information. The test-apparatus temperature controller 121 may confirm the external temperature or humidity. If the external temperature is greater than a general room temperature or a predetermined reference temperature, preheating may be quickly achieved so that the external temperature is maintained at a lower temperature than a general air temperature. As another example, if the external temperature is less than a general room temperature or a predetermined reference temperature, it may take a longer amount of time for preheating, accordingly the external temperature may be maintained at a higher temperature than a general air temperature. As a result, when a user desires to perform testing while simultaneously saving energy, the user can control a current temperature to reach a test temperature within a shorter amount of time.

Examples of methods for controlling the test apparatus are further described herein. The test apparatus 100 described herein may be applied to the following control method of the test apparatus. That is, the examples and drawings of the above-mentioned test apparatus 100 may be applied to the control method of the test apparatus. For example, configurations and the relationship among the test apparatus 100, the air-conditioner 200, and the storage 300, which are used to perform the control method of the test apparatus, are the same as the above-mentioned examples.

FIGS. 21 to 24 are flowcharts illustrating a method for controlling a test apparatus according to various exemplary embodiments.

Figure 21:
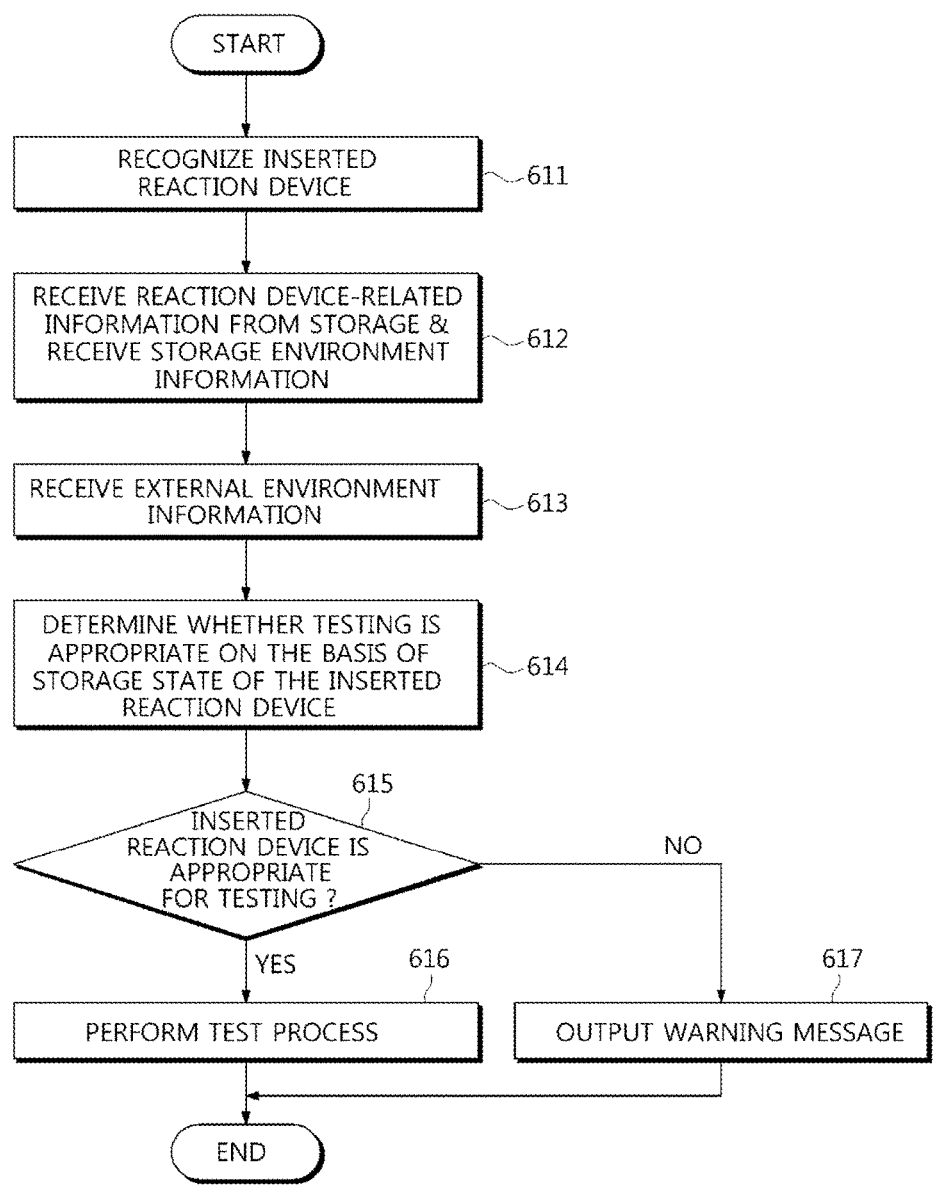
FIGS. 21 to 24 are flowcharts illustrating a method for controlling a test apparatus according to various exemplary embodiments.

FIG. 21 is a flowchart illustrating a method for determining whether the reaction device is appropriate for testing while the reaction device is inserted into the test apparatus.

Referring to FIG. 21, the test apparatus recognizes the inserted reaction device in operation 611. For example, the reader 162 of the test apparatus 100 may read the tag that is attached to the inserted reaction devices (10, 20), and may obtain reaction device information included in the tag. The obtained information may be temporarily or permanently stored in the memory 126.

The reaction device-related information and the storage environment information are received from the storage in operation 612. For example, the test apparatus 100 may request information related to the inserted reaction devices (10, 20) and the storage environment information from the storage 300. As another example, at a specific time at which the reaction devices (10, 20) are released from the storage 300, the storage 300 may also transmit the storage environment information and information about the released reaction devices (10, 20).

The test apparatus 100 receives the external environment information from the external sensor in operation 613. For example, the external environment information may include the external temperature and humidity information. The temperature and humidity data contained in a predetermined time range based on a data transmission time for the test apparatus 100 can be transmitted, and the temperature and humidity information at a specific time may be transmitted.

Although recognition of the reaction device, the reaction device-related information, storage environment information reception, and the external environment information reception are sequentially shown according to characteristics of the flowchart in this example, the sequence of the above operations is not limited to the example of FIG. 21.

The test apparatus determines whether testing is appropriate based on a storage state of the inserted reaction device in operation 614. For example, a first time at which the inserted reaction devices (10, 20) are released from the storage 300 is compared with a second time at which the reaction devices (10, 20) are inserted into the test apparatus 100. Accordingly, the test apparatus 100 may recognize how long the reaction devices (10, 20) are exposed to the outside, and may also determine to which external environment the reaction devices are exposed based on the external temperature and humidity information. The storage 300 may determine which environment is used to store the reaction devices. In addition, at least one of a current temperature and humidity of the reaction devices (10, 20) may also be estimated.

For example, if the reaction devices (10, 20) are stored in the storage 300 at the wrong temperature or humidity, or if the estimated temperature or humidity of the reaction device exceeds a reference range that is appropriate for test execution, this means that the inserted reaction devices (10, 20) may be inappropriate or unsuitable for testing. As another example, if the inserted reaction devices (10, 20) are exposed to the outside for a longer period of time than the recommended time, the inserted reaction devices (10, 20) may be inappropriate or unsuitable for such testing.

Accordingly, if it is determined that the inserted reaction device is appropriate for testing in operation 615, the test process is performed in operation 616. However, if it is determined that the inserted reaction device is inappropriate for such testing in operation 615, a warning message is output in operation 617.

Information about the test process to be performed may be contained in the reaction device information obtained from the tag, and a test process category according to the reaction device category may be pre-stored in the memory 126. According to various exemplary embodiments, to perform the test process, the internal temperature of the test apparatus 100 should be controlled. For example, the internal temperature of the test apparatus 100 may be controlled based on the estimated reaction device temperature and the internal temperature that are sensed by the internal sensor 150 of the test apparatus 100. As described above, the temperature or humidity of the reaction device may be estimated based on a variety of information, i.e., the entry/exit time to/from the storage 300, the storage environment in the storage 300, the amount of time exposed to the outside, and the external environment. As a result, an accurate estimation may be performed so that correct control of the apparatus is possible based on the accurate estimation result. Therefore, the reaction device released from the storage 300 may not be exposed to the outside at room temperature, and may be immediately inserted into the test apparatus 100.

Meanwhile, a warning message that may be generated when the inserted reaction device is inappropriate for testing may be a message commanding replacement of the reaction device as shown in the examples of FIGS. 15 and 16, or may be a message for querying execution or non-execution of the test.

Figure 22:
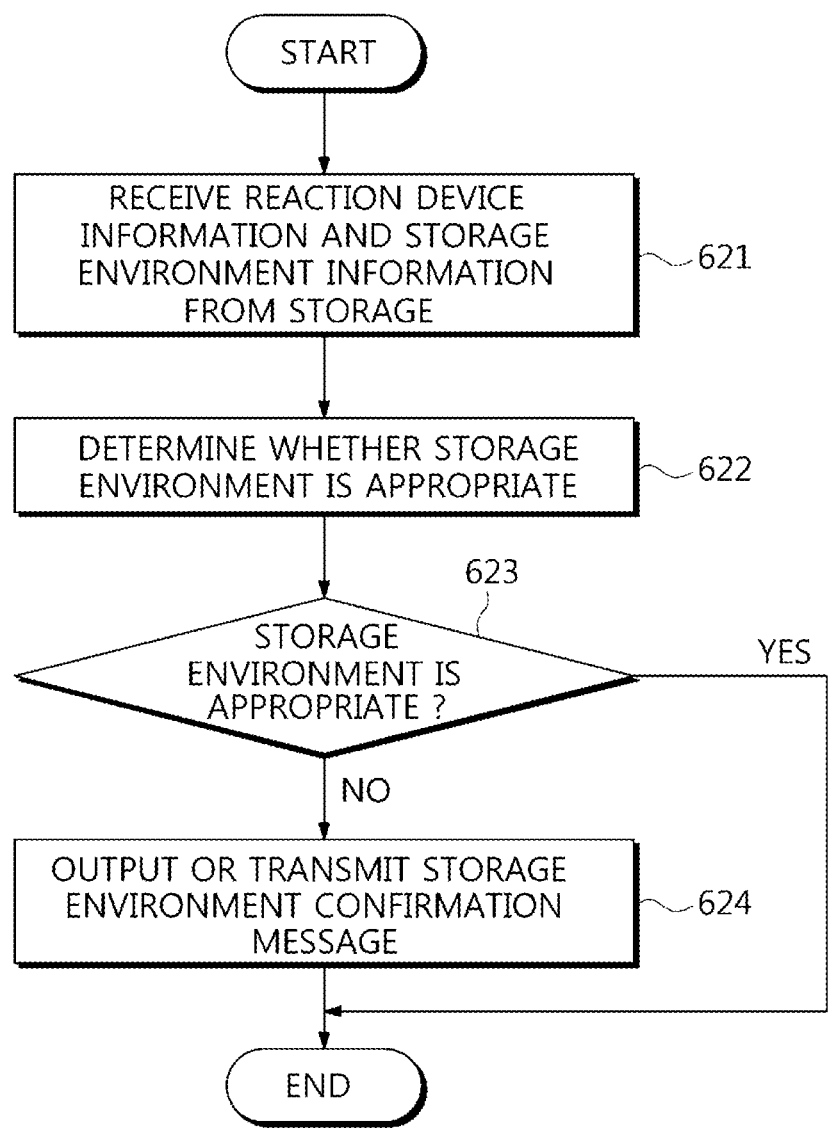
Figure 23:
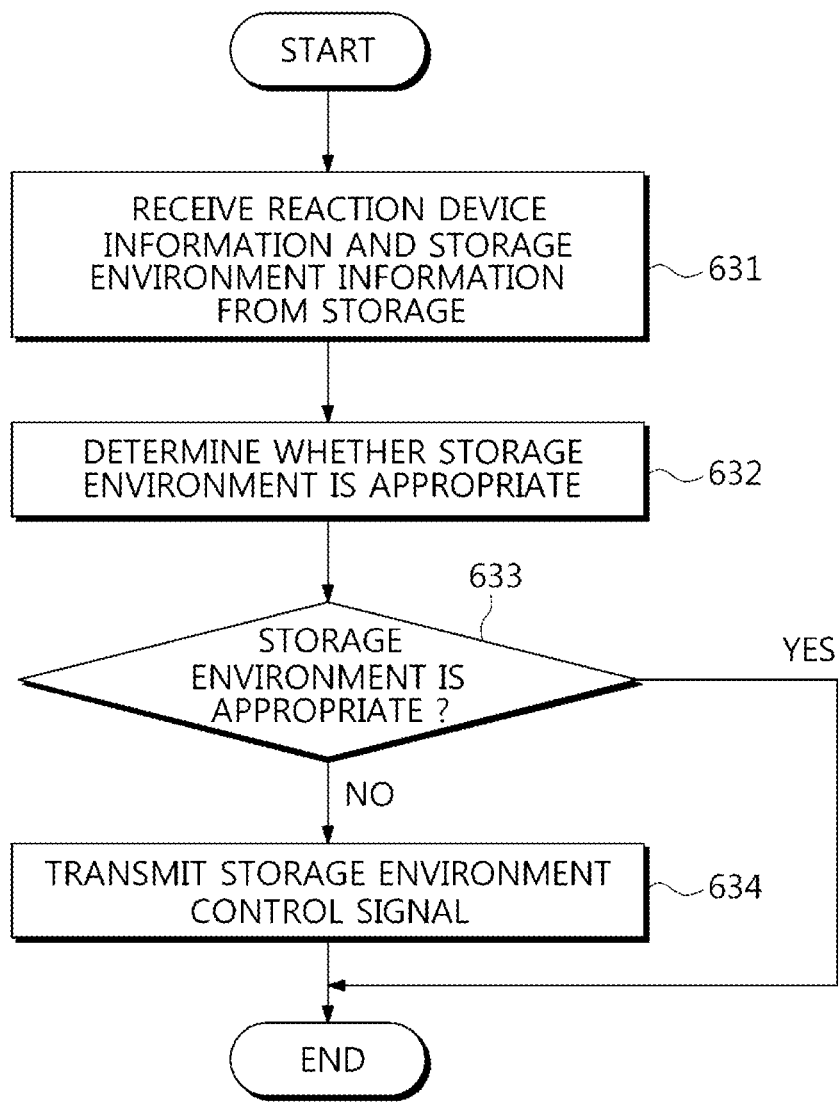

FIGS. 22 and 23 are flowcharts illustrating a method for determining whether the storage environment is appropriate irrespective of whether the reaction device is inserted or not, and a control process for the determination according to various exemplary embodiments.

Referring to FIG. 22, the test apparatus receives the reaction device information and the storage environment information from the storage in operation 621. For example, although the reaction device is not inserted into the test apparatus 100, the storage 300 may periodically transmit the storage environment information and the stored reaction device information to the test apparatus 100.

Next a determination is made as to whether or not the storage environment is appropriate for testing, in operation 622. For example, the storage environment controller 123 of the test apparatus 100 may compare an appropriate temperature and humidity contained in the reaction device information with the internal temperature and humidity (contained in the storage environment information) of the storage 300, to determine whether the storage state is appropriate.

If the storage environment is inappropriate in operation 623, a storage environment confirmation message is output the message indicating the storage environment is inappropriate is transmitted to the pre-registered user mobile device in operation 624.

For example, if the storage environment is inappropriate, the warning screen image 141g may be displayed on the display 141 as shown in FIG. 18. Here, the warning screen image 141g may include a message indicating an abnormal temperature of the storage, a current storage temperature, and a recommended storage temperature. As another example, the information contained in the warning screen image 141g may be transmitted to the pre-registered user mobile device, so that the user can confirm the storage environment. Although the temperature is shown in the example of FIG. 18 for convenience of description, it should be noted that the above-mentioned example can also be applied to the case in which the storage has an abnormal humidity without change.

As another example, as shown in FIG. 23, if the storage environment is inappropriate in operation 633, the test apparatus 100 directly transmits the storage environment control signal in operation 634. In the example of FIG. 23, operations 631 and 632 of FIG. 23 are the same as operations 621 and 622 of FIG. 22.

The above-mentioned example indicates that the test apparatus 100 directly controls the environment including the temperature and humidity of the storage 300, and the environment control signal is applied to the storage 300, so that the storage 300 can be controlled at an appropriate temperature or appropriate humidity.

Figure 24:
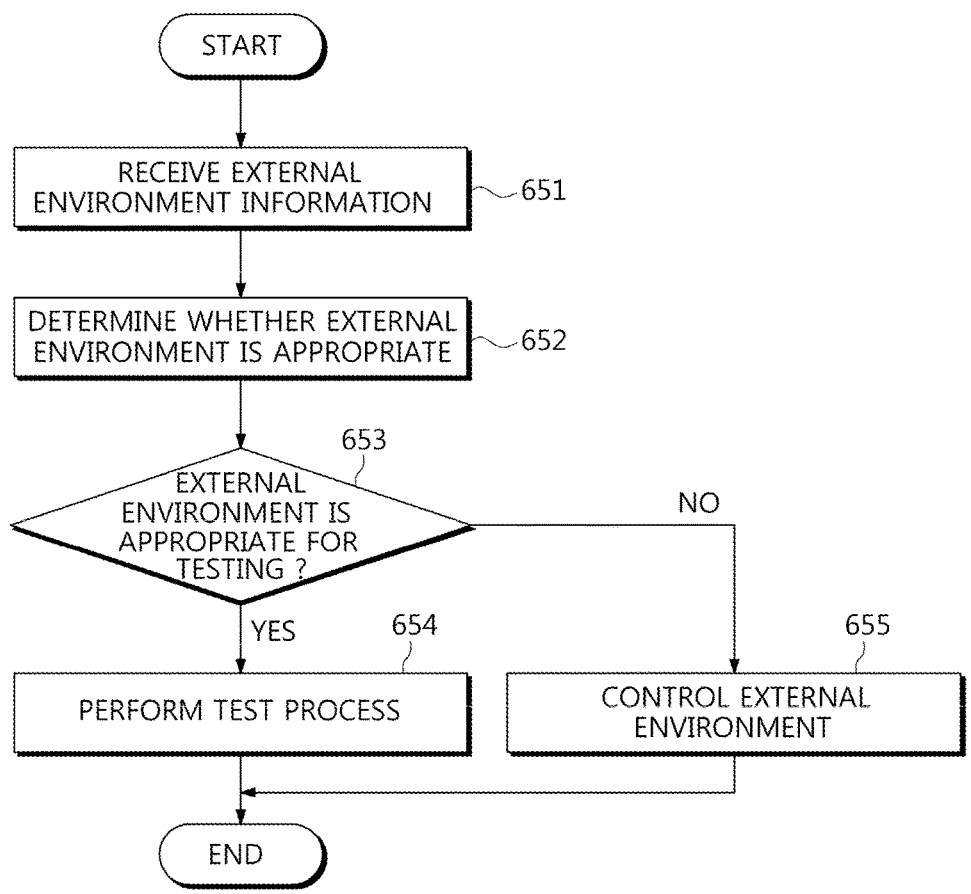

FIG. 24 is a flowchart illustrating a method for controlling the external environment using the test apparatus according to an exemplary embodiment.

Referring to FIG. 24, when testing is completed, or if a standby state for waiting for such testing is given, the test apparatus 100 may allow the external environment to be maintained at the environment that is appropriate for testing. In this example, the test apparatus receives the external environment information including the external temperature and humidity information from the air-conditioner 200 in operation 651.

Accordingly, the test apparatus can determine whether the external environment is appropriate for such testing based on the received external environment information in operation 652.

For example, a reference range for the external temperature or humidity that is appropriate for the standby state may be predetermined. If the received external environment information exceeds the reference range, this refers to an example in which the received external environment is inappropriate for test execution.

As another example, if the external environment is appropriate for testing in operation 653, the test process is carried out in operation 654. If the external environment is inappropriate for testing in operation 653, a control signal is applied to the air-conditioner 200 to control a temperate or a humidity of the external environment in operation 655.

Alternatively, a message indicating the environment in which test execution is not suitable or appropriate may be displayed on the display 141, the testing may be prevented from being executed, and a message indicating such may be applied to the pre-registered mobile device, so that the user can recognize the current control state through the received message.

On the other hand, the internal temperature or humidity of the test apparatus 100 may be controlled in the standby state based on the external environment information. For example, if the external temperature of the test apparatus 100 is higher than a general room temperature or a predetermined reference temperature, preheating can be quickly achieved so that the external temperature is maintained at a lower temperature than a general air temperature. As another example, if the external temperature is less than a general room temperature or a predetermined reference temperature, a longer time may be consumed for preheating, so that the external temperature is maintained at a higher temperature than a general air temperature. As a result, when a user desires to perform testing while simultaneously saving energy, the user may control a current temperature to reach a test temperature within a shorter time.

According to one or more exemplary embodiments, the test apparatus described herein may communicate with a storage unit and an external sensor. Accordingly, the storage environment, the external environment, and a reaction device history may be synthetically used may a test apparatus to maintain or otherwise control a temperature of the reaction device such that an accurate test may be performed by the apparatus. As a result, temperature control for testing can be more precisely performed, and a consistent accurate result can be obtained.

In addition, the temperature or humidity of the test apparatus may be controlled using the external environment information in the standby state, resulting in reduction of energy consumption.

In addition, a plurality of test apparatuses may share only one external sensor, thus reducing the cost of electronic components. Furthermore, if any one of the electronic components malfunctions, the faulty component can be easily replaced with another one.

In addition, if the external environment is inappropriate for test execution due to an inappropriate temperature or humidity, the test apparatus may inform the user of the inappropriate external environment and prevent the test from being executed, so that there is no need to perform unnecessary testing.

In addition, the test apparatus can prevent execution of the reaction device that is determined to be inappropriate for testing, so that it can prevent the occurrence of incorrect or inaccurate test results.

According to one or more exemplary embodiments, the test apparatus and the method for controlling the same may receive information about a reaction device from both a storage storing a sample therein and a sensor sensing the external environment of the test apparatus. Accordingly, the apparatus may receive information regarding the storage environment, and information regarding the external environment, and can perform various control actions for testing the sample based on the received information, thereby increasing reliability of the test result.

Although a few exemplary embodiments of the present invention have been shown and described, it should be appreciated by those skilled in the art that changes may be made in these exemplary embodiments without departing from the principles and spirit of the invention, the scope of which is defined in the claims and their equivalents.

What is claimed is:

1. A test apparatus comprising:
   a communicator configured to receive at least one of storage time information of a reaction device and storage environment information of a storage including the reaction device therein, and to receive external environment information of the test apparatus from an external sensor; and
   a controller configured to determine whether testing of the reaction device is to be performed based on at least one of the storage time information of the reaction device, the environment information of the storage, and the external environment information of the test apparatus;
   wherein the external environment information comprises at least one of external temperature information and humidity information of an area around the test apparatus: and
   wherein the controller is configured to control at least one of an internal temperature and a humidity of the test apparatus in a standby state based the external environment information.

2. The test apparatus according to claim 1, wherein the storage environment information comprises at least one of internal temperature information and humidity information about the storage.

3. The test apparatus according to claim 1, wherein the controller is configured to estimate at least one of a temperature and a humidity of the reaction device based on the storage time information of the reaction device, the storage environment information of the storage, and the external environment information, and
   the controller is configured to determine whether testing of the reaction device is to be performed based on the estimated at least one of the temperature and the humidity of the reaction device.

4. The test apparatus according to claim 3, wherein the controller is configured to compare at least one of the estimated temperature and humidity of the reaction device with a predetermined reference value, and determine whether the at least one of temperature and humidity of the reaction device is in a reference range based on the comparison.

5. The test apparatus according to claim 4, further comprising:
   a display configured to display a warning screen image in response to at least one of the estimated temperature and humidity of the reaction device exceeding the reference range.

6. The test apparatus according to claim 4, wherein the controller is configured to prevent testing of the reaction device in response to at least one of the estimated temperature and humidity of the reaction device exceeding the reference range.

7. The test apparatus according to claim 3, wherein the controller is configured to control an internal temperature of the test apparatus to be a temperature appropriate for a test process applied to the reaction device based on an estimated reaction device temperature.

8. The test apparatus according to claim 1, wherein the controller is configured to prevent testing of the reaction device in response to at least one of the external temperature and the humidity of the reaction device exceeding a reference range.

9. The test apparatus according to claim 1, wherein the controller is configured to determine a storage state of the reaction device based on the storage time information of the reaction device and the storage environment information, and prevent testing of the reaction device in response to the storage state of the reaction device being determined as inappropriate.

10. The test apparatus according to claim 1, wherein the controller is configured to determine an exposed time of the reaction device and information about the exposed external environment based on the storage information of the reaction device and the external environment information of the test apparatus.

11. The test apparatus according to claim 10, further comprising:
    a display configured to display the exposed time of the reaction device and the information about the exposed external environment.

12. The test apparatus according to claim 1, wherein the controller is configured to compare information about a recommended storage environment of the reaction device stored in the storage with the storage environment information, and determine whether the storage environment information matches the recommended storage environment of the reaction device.

13. The test apparatus according to claim 12, wherein the controller is configured to transmit a control signal for controlling at least one of a temperature and a humidity of the storage to the storage, in response to the storage environment information not matching the recommended storage environment of the reaction device.

14. The test apparatus according to claim 12, wherein the controller is configured to transmit a warning message to a pre-registered mobile device of a user when the storage environment information not matching the recommended storage environment of the reaction device.

15. The test apparatus according to claim 1, wherein the controller is configured to transmit a control signal for controlling an external environment to an air-conditioner that is located externally from the test apparatus, in response to the external environment information exceeding a predetermined reference range.

16. The test apparatus according to claim 1, wherein the communicator is further configured to receive, from the storage, information about the reaction device comprising at least one of identification (ID) information of the reaction device, information about a recommended storage environment of the reaction device, and information about a test process applied to the reaction device.

17. The test apparatus according to claim 16, further comprising:
    a reader configured to, in response to the reaction device being inserted into the test apparatus, obtain the reaction device information from a tag attached to the inserted reaction device.

18. A method for controlling a test apparatus, the method comprising:
    acquiring information of a reaction device;
    receiving at least one of storage time information of the reaction device and storage environment information of a storage, and receiving external environment information of the test apparatus from an external sensor;

determining whether testing of the reaction device is to be performed based on at least one of the storage time information of the reaction device, the environment information of the storage, and the external environment information of the test apparatus, wherein the determining whether testing of the reaction device is to be performed comprises estimating at least one of a temperature and a humidity of the reaction device based on at least one of the storage time information of the reaction device, the storage environment information, and the external environment information; and controlling an internal temperature of the test apparatus to be a temperature appropriate for a test process applied to the reaction device based on the estimated temperature of the reaction device in response to testing of the reaction device being determined to be performed, wherein the external environment information comprises at least one of external temperature information and humidity information of the test apparatus.

19. The method according to claim 18, wherein the reaction device information comprises at least one of identification (ID) information of the reaction device, information about a recommended storage environment of the reaction device, and information about a test process applied to the reaction device.

20. The method according to claim 18, wherein the storage environment information comprises at least one of internal temperature information and humidity information of the storage.

21. The method according to claim 18, wherein the determining whether testing of the reaction device is to be performed comprises:

comparing at least one of the estimated temperature and humidity of the reaction device with a predetermined reference value, and determining whether at least one of the estimated temperature and humidity of the reaction device is within a reference range.

22. The method according to claim 21, further comprising:

displaying a warning screen image in response to at least one of the estimated temperature and humidity of the reaction device exceeding the reference range.

23. The method according to claim 21, further comprising:

preventing testing of the reaction device in response to at least one of the estimated temperature and humidity of the reaction device exceeding the reference range.

24. The method according to claim 18, wherein the determining whether testing of the reaction device is to be performed comprises:

determining a storage state of the reaction device based on the storage time information of the reaction device and the storage environment information.

25. The method according to claim 18, wherein the determining whether testing of the reaction device is to be performed comprises:

determining an exposed time of the reaction device and information about the exposed external environment based on the storage time information of the reaction device and the external environment information.

26. The method according to claim 18, wherein the acquiring the reaction device information comprises:

in response to the reaction device being inserted into the test apparatus, acquiring the reaction device information from a tag attached to the inserted reaction device.

* * * * *